United States Patent
Sibbitt, Jr. et al.

(10) Patent No.: US 8,758,397 B2
(45) Date of Patent: Jun. 24, 2014

(54) VASCULAR CLOSURE METHODS AND APPARATUSES

(75) Inventors: Wilmer L. Sibbitt, Jr., Albuquerque, NM (US); Randy R. Sibbitt, Helena, MT (US)

(73) Assignee: Abbott Vascular Inc., Santa Clara, CA (US)

( * ) Notice: Subject to any disclaimer, the term of this patent is extended or adjusted under 35 U.S.C. 154(b) by 1209 days.

(21) Appl. No.: 11/508,656

(22) Filed: Aug. 23, 2006

(65) Prior Publication Data

US 2007/0049967 A1 Mar. 1, 2007

Related U.S. Application Data

(63) Continuation-in-part of application No. 11/316,775, filed on Dec. 23, 2005, now abandoned.

(60) Provisional application No. 60/711,279, filed on Aug. 24, 2005.

(51) Int. Cl.
*A61B 17/08* (2006.01)
*A61D 1/00* (2006.01)

(52) U.S. Cl.
USPC ............ 606/213; 606/219; 606/151; 606/142

(58) Field of Classification Search
USPC ......... 606/139, 140, 142, 144, 149, 151, 157, 606/213, 215, 216, 219–221, 232
See application file for complete search history.

(56) References Cited

U.S. PATENT DOCUMENTS

| | | | |
|---|---|---|---|
| 2,108,206 A | 2/1938 | Meeker | |
| 2,371,978 A | 3/1945 | Perham | |
| 2,610,631 A | 9/1952 | Calicchio | |
| 3,814,104 A | 6/1974 | Irnich et al. | |
| 3,856,018 A | 12/1974 | Perisse et al. | |
| 3,874,388 A | 4/1975 | King et al. | |
| 3,908,662 A * | 9/1975 | Razgulov et al. | 606/149 |
| 3,926,194 A | 12/1975 | Greenberg et al. | |

(Continued)

FOREIGN PATENT DOCUMENTS

| | | |
|---|---|---|
| FR | 2768324 | 3/1999 |
| JP | 2000014634 | 1/2000 |

(Continued)

OTHER PUBLICATIONS

International Search Report for PCT/US06/33033 dated Sep. 28, 2007.

(Continued)

*Primary Examiner* — Dianne Dornbusch

(74) *Attorney, Agent, or Firm* — Workman Nydegger; Randy Shen

(57) ABSTRACT

A vascular closure device comprising a retrievable sheath-delivered contractible, clip device with structural radial or terminal members with terminal and non-terminal hooks that engage the vessel wall. Unlike other vascular closure clips, this device is delivered on the outside rather than the inside of sheath. Closure of the tissue opening can be effected by the feet of the clip engaging the puncture, aperture, or wound edges and memory characteristics of the device cause a contraction of the members, bringing the members into apposition and the wound edges together, permitting immediate vascular closure and healing of the blood vessel. The device can be delivered and recovered by an intravascular sheath.

20 Claims, 21 Drawing Sheets

(56) References Cited

U.S. PATENT DOCUMENTS

| | | | | |
|---|---|---|---|---|
| 3,939,820 A | | 2/1976 | Grayzel | |
| 3,985,138 A | | 10/1976 | Jarvik | |
| 4,011,872 A | | 3/1977 | Komiya | |
| 4,018,228 A | | 4/1977 | Goosen | |
| 4,018,229 A | | 4/1977 | Komiya | |
| 4,501,276 A | | 2/1985 | Lombardi | |
| 4,830,002 A | | 5/1989 | Semm | |
| 5,041,129 A | | 8/1991 | Hayhurst et al. | |
| 5,059,201 A | | 10/1991 | Asnis | |
| 5,100,422 A | | 3/1992 | Berguer et al. | |
| 5,176,691 A | | 1/1993 | Pierce | |
| 5,192,287 A | | 3/1993 | Fournier et al. | |
| 5,217,471 A | | 6/1993 | Burkhart | |
| 5,237,996 A | | 8/1993 | Waldman | |
| 5,254,105 A | | 10/1993 | Haaga | |
| 5,290,284 A | | 3/1994 | Adair | |
| 5,330,445 A | | 7/1994 | Haaga | |
| 5,336,231 A | | 8/1994 | Adair | |
| 5,354,279 A | | 10/1994 | Hofling | |
| 5,383,905 A | | 1/1995 | Golds et al. | |
| 5,403,330 A | | 4/1995 | Tuason | |
| 5,403,331 A | | 4/1995 | Chesterfield et al. | |
| 5,425,740 A | | 6/1995 | Hutchinson, Jr. | |
| 5,462,561 A | | 10/1995 | Voda | |
| 5,466,241 A | | 11/1995 | Leroy et al. | |
| 5,478,353 A | | 12/1995 | Yoon | |
| 5,478,354 A | * | 12/1995 | Tovey et al. | 606/219 |
| 5,492,119 A | | 2/1996 | Abrams | |
| 5,507,744 A | | 4/1996 | Tay et al. | |
| 5,536,267 A | | 7/1996 | Edwards | |
| 5,562,684 A | | 10/1996 | Kammerer | |
| 5,571,120 A | | 11/1996 | Yoon | |
| 5,573,540 A | | 11/1996 | Yoon | |
| 5,609,597 A | | 3/1997 | Lehner | |
| 5,613,974 A | | 3/1997 | Andreas et al. | |
| 5,613,975 A | | 3/1997 | Christy | |
| 5,643,318 A | | 7/1997 | Tsukernik et al. | |
| 5,647,372 A | | 7/1997 | Tovey et al. | |
| 5,649,959 A | | 7/1997 | Hannam et al. | |
| 5,672,174 A | | 9/1997 | Gough et al. | |
| 5,674,231 A | * | 10/1997 | Green et al. | 606/142 |
| 5,693,061 A | | 12/1997 | Pierce et al. | |
| 5,713,899 A | * | 2/1998 | Marnay et al. | 623/17.11 |
| 5,728,143 A | | 3/1998 | Gough et al. | |
| 5,759,189 A | | 6/1998 | Ferragamo et al. | |
| 5,766,217 A | | 6/1998 | Christy | |
| 5,782,861 A | | 7/1998 | Cragg et al. | |
| 5,792,151 A | | 8/1998 | Heck et al. | |
| 5,797,928 A | | 8/1998 | Kogasaka | |
| 5,797,929 A | | 8/1998 | Andreas et al. | |
| 5,810,845 A | | 9/1998 | Yoon | |
| 5,814,052 A | | 9/1998 | Nakao et al. | |
| 5,817,113 A | | 10/1998 | Gifford, III et al. | |
| 5,855,576 A | | 1/1999 | LeVeen et al. | |
| 5,861,005 A | | 1/1999 | Kontos | |
| 5,865,791 A | | 2/1999 | Whayne et al. | |
| 5,873,876 A | | 2/1999 | Christy | |
| 5,897,487 A | | 4/1999 | Ouchi | |
| 5,906,631 A | | 5/1999 | Imran | |
| 5,919,207 A | | 7/1999 | Taheri | |
| 5,951,547 A | | 9/1999 | Gough et al. | |
| 5,957,936 A | | 9/1999 | Yoon et al. | |
| 5,957,938 A | | 9/1999 | Zhu et al. | |
| 5,964,782 A | | 10/1999 | Lafontaine et al. | |
| 5,972,009 A | | 10/1999 | Fortier et al. | |
| 5,976,161 A | | 11/1999 | Kirsch et al. | |
| 5,980,517 A | | 11/1999 | Gough et al. | |
| 5,984,950 A | | 11/1999 | Cragg et al. | |
| 5,993,466 A | | 11/1999 | Yoon | |
| 5,993,476 A | * | 11/1999 | Groiso | 606/219 |
| 6,009,877 A | | 1/2000 | Edwards | |
| 6,022,372 A | | 2/2000 | Kontos | |
| 6,024,747 A | | 2/2000 | Kontos | |
| 6,056,744 A | | 5/2000 | Edwards | |
| 6,059,719 A | | 5/2000 | Yamamoto et al. | |
| 6,068,603 A | | 5/2000 | Suzuki | |
| 6,083,242 A | * | 7/2000 | Cook | 606/219 |
| 6,120,524 A | | 9/2000 | Taheri | |
| 6,126,675 A | | 10/2000 | Shchervinsky et al. | |
| 6,136,010 A | | 10/2000 | Modesitt et al. | |
| 6,143,004 A | | 11/2000 | Davis | |
| 6,152,936 A | | 11/2000 | Christy et al. | |
| 6,165,204 A | | 12/2000 | Levinson et al. | |
| 6,197,042 B1 | * | 3/2001 | Ginn et al. | 606/213 |
| 6,221,084 B1 | | 4/2001 | Fleenor | |
| 6,248,124 B1 | | 6/2001 | Pedros et al. | |
| 6,296,657 B1 | | 10/2001 | Brucker | |
| 6,306,081 B1 | | 10/2001 | Ishikawa et al. | |
| 6,322,580 B1 | * | 11/2001 | Kanner | 606/213 |
| 6,358,258 B1 | | 3/2002 | Arcia et al. | |
| 6,395,015 B1 | | 5/2002 | Borst et al. | |
| 6,397,110 B1 | | 5/2002 | Kuzma | |
| 6,428,472 B1 | | 8/2002 | Haas | |
| 6,443,963 B1 | | 9/2002 | Baldwin et al. | |
| 6,461,366 B1 | | 10/2002 | Seguin | |
| 6,482,224 B1 | | 11/2002 | Michler et al. | |
| 6,517,498 B1 | | 2/2003 | Burbank et al. | |
| 6,533,812 B2 | * | 3/2003 | Swanson et al. | 623/1.23 |
| 6,547,806 B1 | | 4/2003 | Ding | |
| 6,569,159 B1 | | 5/2003 | Edwards et al. | |
| 6,569,185 B2 | | 5/2003 | Ungs | |
| 6,572,629 B2 | | 6/2003 | Kalloo et al. | |
| 6,610,072 B1 | | 8/2003 | Christy et al. | |
| 6,613,060 B2 | | 9/2003 | Adams et al. | |
| 6,623,509 B2 | | 9/2003 | Ginn | |
| 6,623,510 B2 | | 9/2003 | Carley et al. | |
| 6,663,655 B2 | | 12/2003 | Ginn et al. | |
| 6,676,685 B2 | | 1/2004 | Pedros et al. | |
| 6,679,904 B2 | | 1/2004 | Gleeson et al. | |
| 6,689,051 B2 | | 2/2004 | Nakada et al. | |
| 6,695,867 B2 | | 2/2004 | Ginn et al. | |
| 6,743,195 B2 | | 6/2004 | Zucker | |
| 6,743,259 B2 | | 6/2004 | Ginn | |
| 6,745,079 B2 | | 6/2004 | King | |
| 6,746,457 B2 | | 6/2004 | Dana et al. | |
| 6,749,621 B2 | | 6/2004 | Pantages et al. | |
| 6,749,622 B2 | | 6/2004 | McGuckin, Jr. et al. | |
| 6,767,356 B2 | * | 7/2004 | Kanner et al. | 606/213 |
| 6,776,785 B1 | * | 8/2004 | Yencho et al. | 606/153 |
| 6,837,906 B2 | | 1/2005 | Ginn | |
| 6,846,319 B2 | | 1/2005 | Ginn et al. | |
| 6,890,343 B2 | | 5/2005 | Ginn et al. | |
| 6,896,692 B2 | | 5/2005 | Ginn et al. | |
| 6,969,397 B2 | | 11/2005 | Ginn | |
| 7,048,747 B2 | | 5/2006 | Arcia et al. | |
| 7,060,084 B1 | * | 6/2006 | Loshakove et al. | 606/213 |
| 7,063,661 B2 | | 6/2006 | Okada | |
| 7,063,711 B1 | * | 6/2006 | Loshakove et al. | 606/153 |
| 7,083,635 B2 | | 8/2006 | Ginn | |
| 7,112,225 B2 | | 9/2006 | Ginn | |
| 7,122,002 B2 | | 10/2006 | Okada | |
| 7,147,646 B2 | | 12/2006 | Dana et al. | |
| 7,270,672 B1 | | 9/2007 | Singer | |
| 7,316,704 B2 | | 1/2008 | Bagaoisan et al. | |
| 7,326,230 B2 | | 2/2008 | Ravikumar | |
| 7,331,979 B2 | | 2/2008 | Khosravi et al. | |
| 7,335,220 B2 | | 2/2008 | Khosravi et al. | |
| 7,338,514 B2 | | 3/2008 | Wahr et al. | |
| 7,361,183 B2 | | 4/2008 | Ginn | |
| 7,361,185 B2 | | 4/2008 | O'Malley et al. | |
| 7,393,363 B2 | | 7/2008 | Ginn | |
| 7,396,359 B1 | | 7/2008 | Derowe et al. | |
| 7,431,727 B2 | * | 10/2008 | Cole et al. | 606/153 |
| 7,507,200 B2 | | 3/2009 | Okada | |
| 7,648,493 B2 | | 1/2010 | Forsberg et al. | |
| 7,727,249 B2 | | 6/2010 | Rahmani | |
| 7,731,655 B2 | | 6/2010 | Smith et al. | |
| 7,749,249 B2 | | 7/2010 | Gelbart et al. | |
| 7,901,428 B2 | | 3/2011 | Ginn et al. | |
| 2001/0046518 A1 | | 11/2001 | Sawhney | |
| 2001/0053909 A1 | | 12/2001 | Nakada | |
| 2002/0099389 A1 | * | 7/2002 | Michler et al. | 606/139 |
| 2002/0106409 A1 | | 8/2002 | Sawhney et al. | |
| 2002/0188275 A1 | | 12/2002 | McGuckin et al. | |

(56) References Cited

U.S. PATENT DOCUMENTS

| | | | |
|---|---|---|---|
| 2003/0187457 A1 | 10/2003 | Weber | |
| 2003/0233095 A1* | 12/2003 | Urbanski et al. | 606/72 |
| 2004/0009205 A1 | 1/2004 | Sawhney | |
| 2004/0093027 A1 | 5/2004 | Fabisiak et al. | |
| 2004/0098044 A1 | 5/2004 | Van de Moer et al. | |
| 2004/0122349 A1 | 6/2004 | Lafontaine et al. | |
| 2004/0127940 A1 | 7/2004 | Ginn et al. | |
| 2004/0143290 A1 | 7/2004 | Brightbill | |
| 2004/0158127 A1 | 8/2004 | Okada | |
| 2004/0158287 A1 | 8/2004 | Cragg et al. | |
| 2004/0167511 A1 | 8/2004 | Buehlmann et al. | |
| 2004/0191277 A1 | 9/2004 | Sawhney et al. | |
| 2004/0215232 A1 | 10/2004 | Belhe et al. | |
| 2004/0225194 A1 | 11/2004 | Smith et al. | |
| 2004/0236354 A1 | 11/2004 | Seguin | |
| 2004/0267193 A1 | 12/2004 | Bagaoisan et al. | |
| 2004/0267308 A1 | 12/2004 | Bagaoisan et al. | |
| 2005/0010248 A1 | 1/2005 | Lafontaine | |
| 2005/0033359 A1 | 2/2005 | Dycus | |
| 2005/0075665 A1* | 4/2005 | Brenzel et al. | 606/213 |
| 2005/0085851 A1 | 4/2005 | Fiehler et al. | |
| 2005/0085854 A1 | 4/2005 | Ginn | |
| 2005/0085855 A1 | 4/2005 | Forsberg | |
| 2005/0090859 A1 | 4/2005 | Ravlkumar | |
| 2005/0121042 A1 | 6/2005 | Belhe et al. | |
| 2005/0149117 A1 | 7/2005 | Khosravi et al. | |
| 2005/0177189 A1 | 8/2005 | Ginn et al. | |
| 2005/0222614 A1 | 10/2005 | Ginn et al. | |
| 2005/0234396 A1 | 10/2005 | Forsberg et al. | |
| 2005/0245876 A1 | 11/2005 | Khosravi et al. | |
| 2005/0256532 A1 | 11/2005 | Nayak et al. | |
| 2005/0261708 A1 | 11/2005 | Pasricha et al. | |
| 2005/0267528 A1 | 12/2005 | Ginn et al. | |
| 2005/0273137 A1 | 12/2005 | Ginn | |
| 2006/0034930 A1 | 2/2006 | Khosravi et al. | |
| 2006/0047313 A1 | 3/2006 | Khanna et al. | |
| 2006/0089635 A1 | 4/2006 | Young et al. | |
| 2006/0095029 A1 | 5/2006 | Young et al. | |
| 2006/0100664 A1 | 5/2006 | Pai et al. | |
| 2006/0106420 A1 | 5/2006 | Dolan et al. | |
| 2006/0253037 A1 | 11/2006 | Ginn et al. | |
| 2006/0253072 A1 | 11/2006 | Pai et al. | |
| 2006/0259049 A1* | 11/2006 | Harada et al. | 606/151 |
| 2007/0049968 A1 | 3/2007 | Sibbitt, Jr. et al. | |
| 2007/0060895 A1 | 3/2007 | Sibbitt, Jr. et al. | |
| 2007/0060950 A1 | 3/2007 | Khosravi et al. | |
| 2007/0083231 A1 | 4/2007 | Lee | |
| 2007/0123817 A1 | 5/2007 | Khosravi et al. | |
| 2007/0198058 A1 | 8/2007 | Gelbart et al. | |
| 2007/0203506 A1 | 8/2007 | Sibbitt, Jr. et al. | |
| 2008/0009794 A1 | 1/2008 | Bagaoisan et al. | |
| 2008/0045979 A1 | 2/2008 | Ma | |
| 2008/0065151 A1 | 3/2008 | Ginn | |
| 2008/0065152 A1 | 3/2008 | Carley | |
| 2008/0287967 A1 | 11/2008 | Andreas et al. | |
| 2009/0088794 A1 | 4/2009 | LaFontaine | |
| 2009/0254119 A1 | 10/2009 | Sibbitt, Jr. et al. | |
| 2010/0130965 A1 | 5/2010 | Sibbitt, Jr. et al. | |
| 2010/0234884 A1 | 9/2010 | Lafontaine et al. | |

FOREIGN PATENT DOCUMENTS

| | | |
|---|---|---|
| JP | 2005218868 A | 8/2005 |
| WO | WO 96/40356 | 12/1996 |
| WO | WO 02062234 | 8/2002 |
| WO | WO 03094748 | 11/2003 |
| WO | WO 2005000126 | 1/2005 |
| WO | WO 2005041782 | 5/2005 |
| WO | WO 2005063129 | 7/2005 |
| WO | WO 2005/092204 | 10/2005 |
| WO | WO 2005112782 | 12/2005 |
| WO | WO 2006026116 | 3/2006 |
| WO | WO 2006052611 | 5/2006 |
| WO | WO 2006052612 | 5/2006 |
| WO | WO 2006078578 | 7/2006 |
| WO | WO 2006115901 | 11/2006 |
| WO | WO 2006115904 | 11/2006 |
| WO | WO 2006118877 | 11/2006 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2010/031050 | 3/2010 |

OTHER PUBLICATIONS

International Search Report for PCT/US06/33031 dated May 19, 2008.
International Search Report for PCT/US06/33032 dated Sep. 27, 2007.
U.S. Appl. No. 60/711,279, filed Aug. 24, 2005, Sibbitt, Jr. et al.
U.S. Appl. No. 60/726,985, filed Oct. 14, 2005, Sibbitt Jr. et al.
U.S. Appl. No. 61/097,072, filed Sep. 15, 2008, Sibbitt Jr. et al.
U.S. Appl. No. 11/316,775, filed Apr. 16, 2008, Office Action.
U.S. Appl. No. 11/316,775, filed Aug. 6, 2008, Office Action.
U.S. Appl. No. 11/508,662, filed Dec. 28, 2009, Restriction Requirement.
U.S. Appl. No. 11/508,662, filed Apr. 14, 2010, Office Action.
U.S. Appl. No. 11/508,662, filed Oct. 26, 2010, Office Action.
U.S. Appl. No. 11/508,715, filed Jan. 6, 2010, Restriction Requirement.
U.S. Appl. No. 11/508,715, filed Apr. 26, 2010, Office Action.
U.S. Appl. No. 11/508,715, filed Oct. 18, 2010, Office Action.
U.S. Appl. No. 12/365,397, filed Sep. 13, 2013, Restriction Requirement.
U.S. Appl. No. 12/559,377, filed Feb. 27, 2012, Office Action.
U.S. Appl. No. 12/365,397, filed Jun. 21, 2011, Notice of Allowance.
U.S. Appl. No. 12/559,377, filed Aug. 3, 2012, Office Action.
U.S. Appl. No. 12/559,377, filed Dec. 14, 2011, Restriction Requirement.
U.S. Appl. No. 12/365,397, filed Oct. 12, 2011, Issue Notification.

* cited by examiner

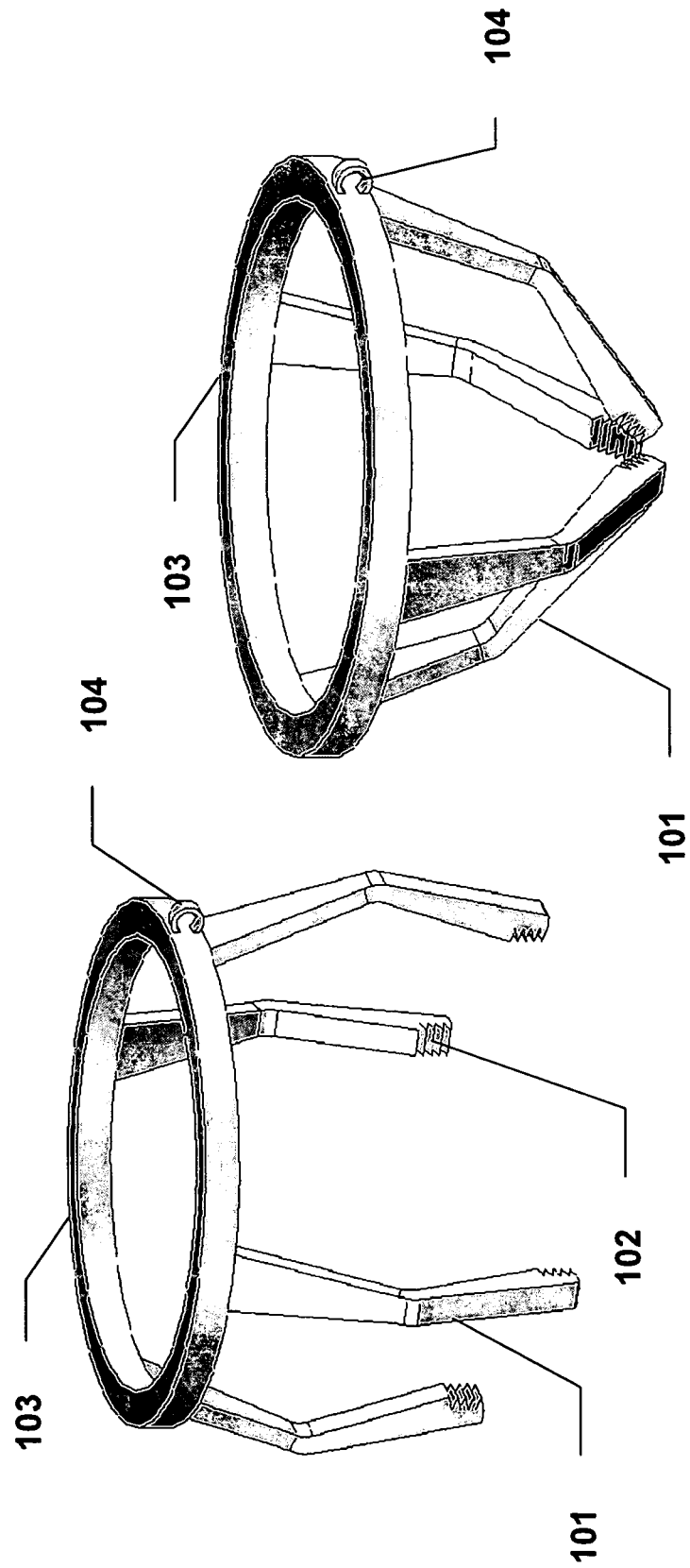

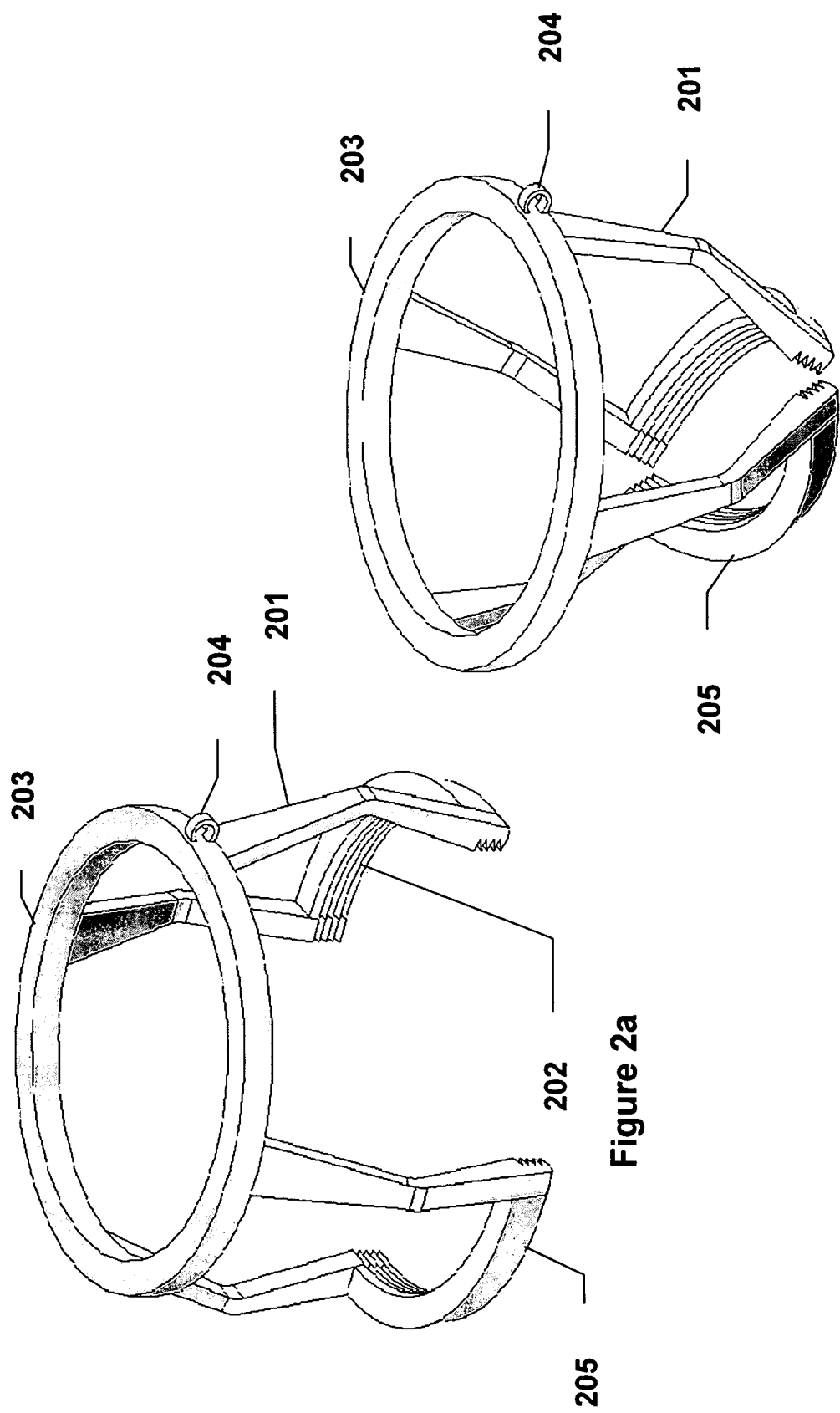

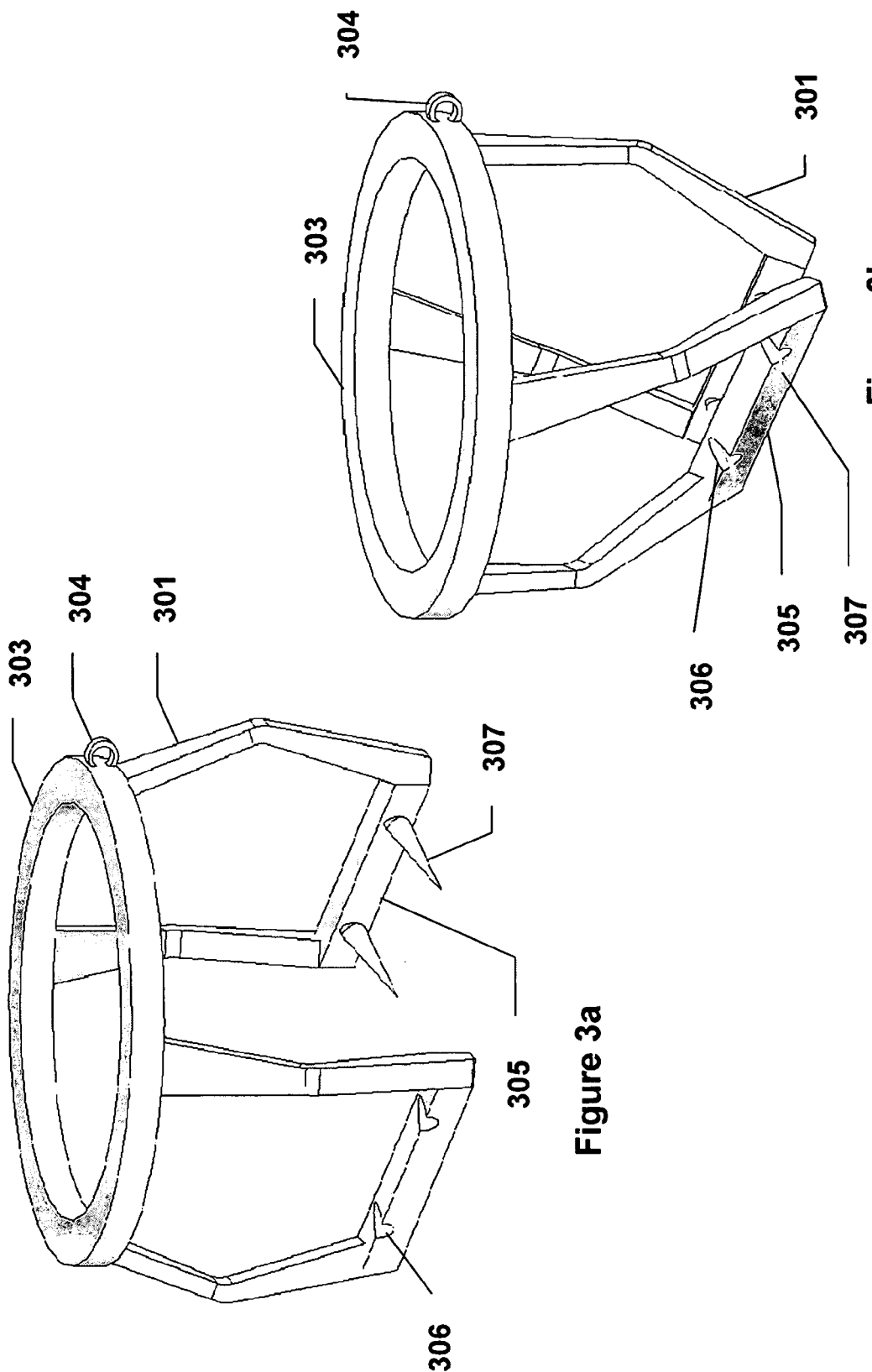

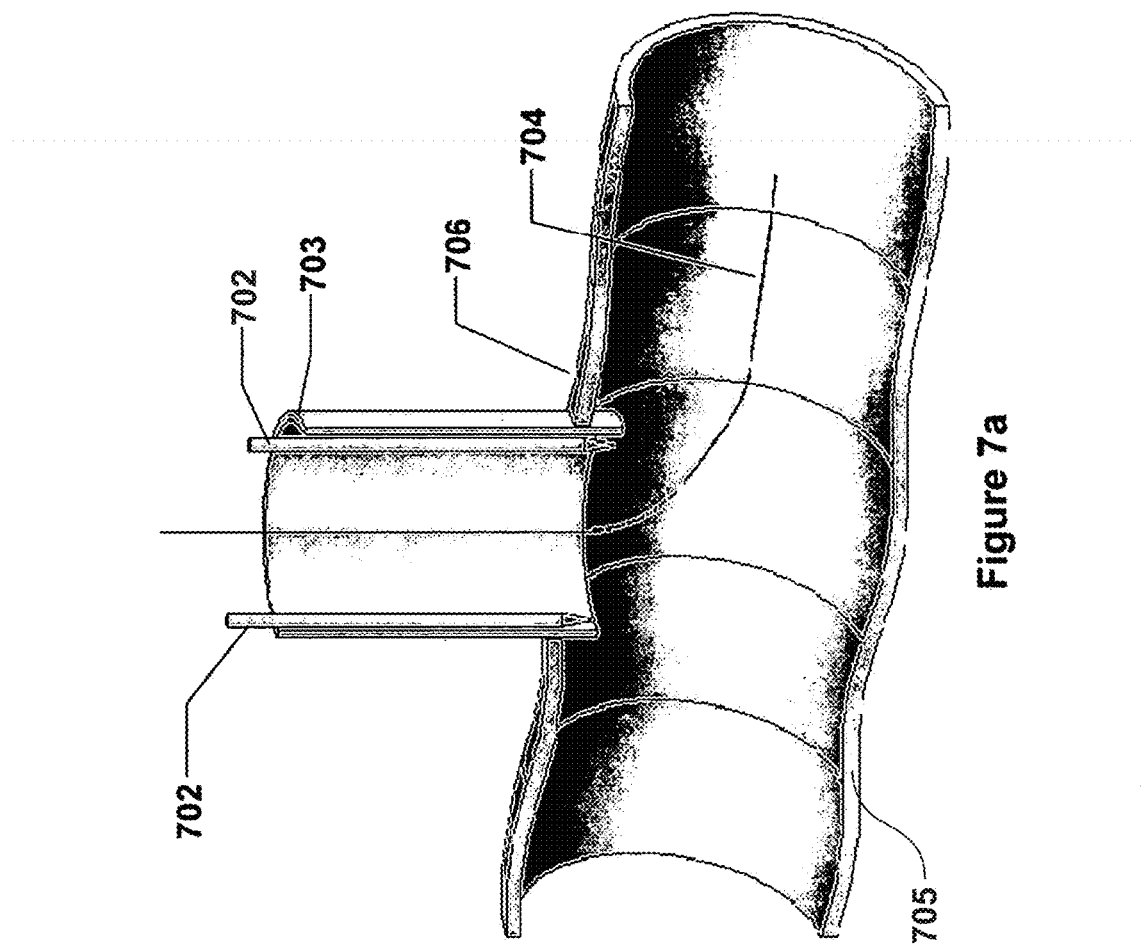

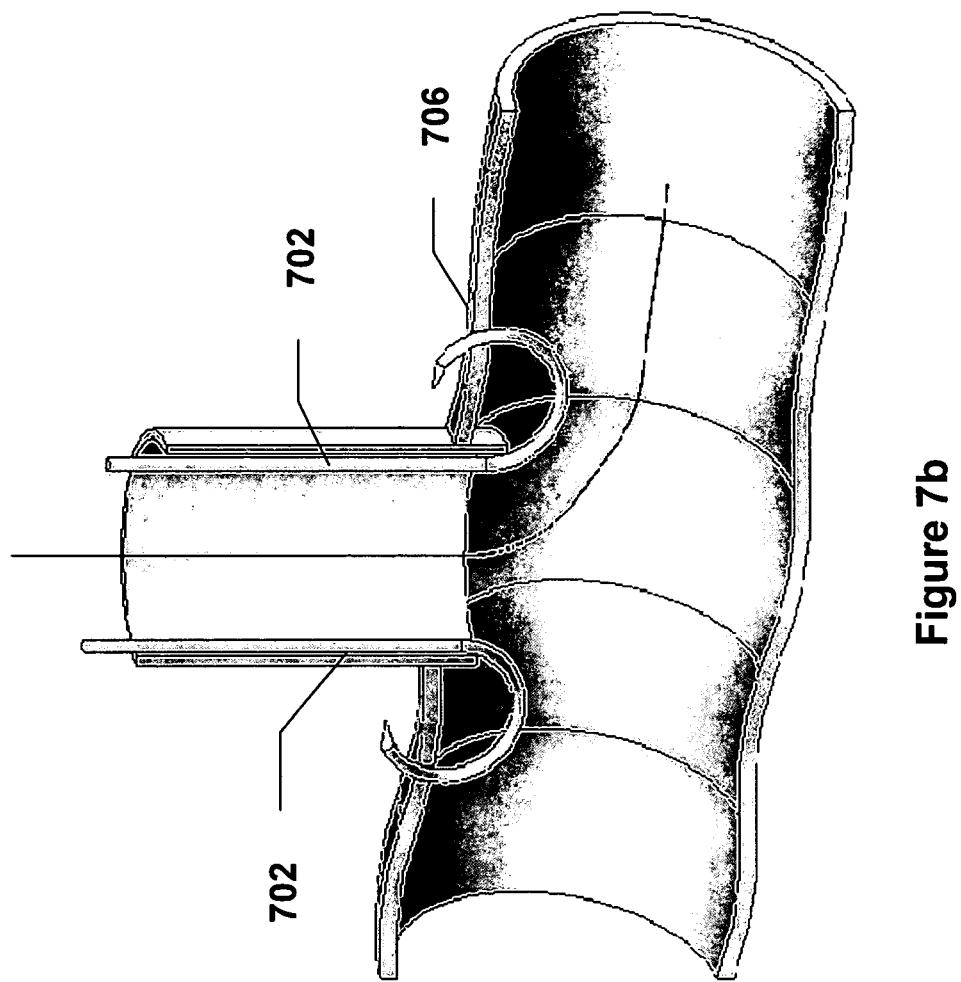

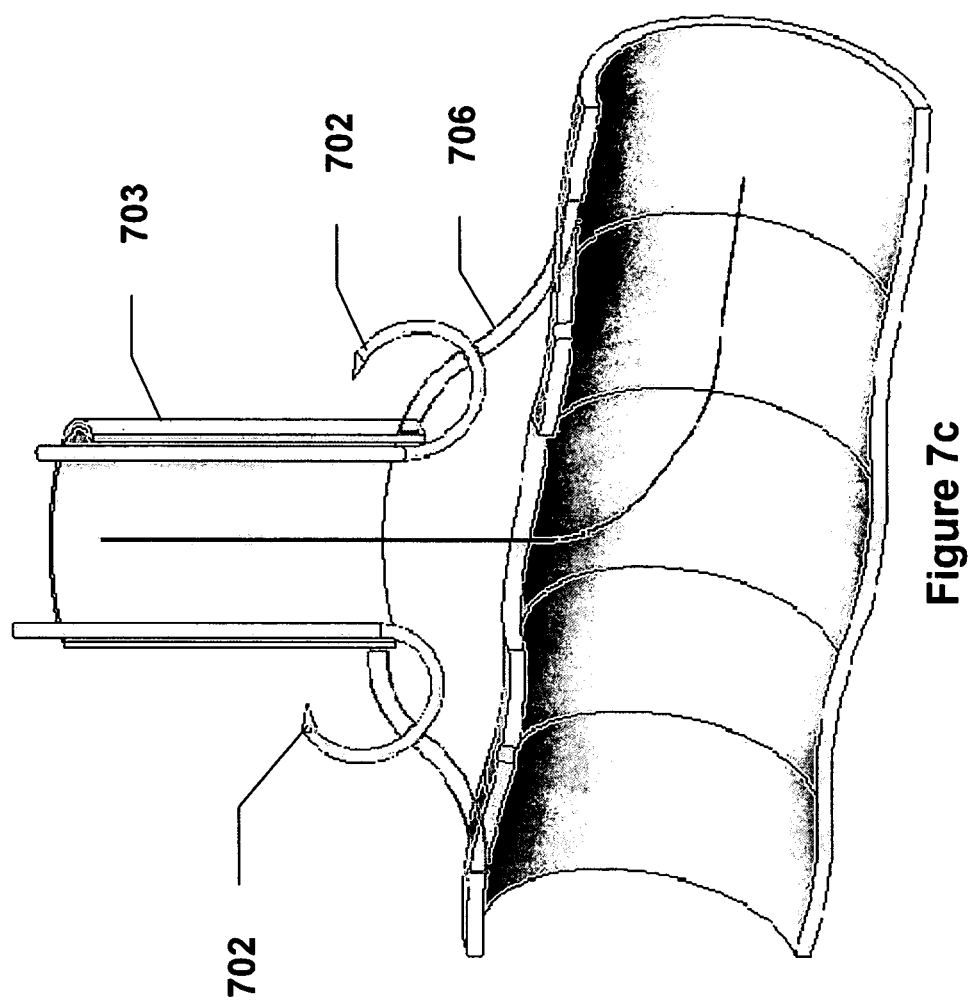

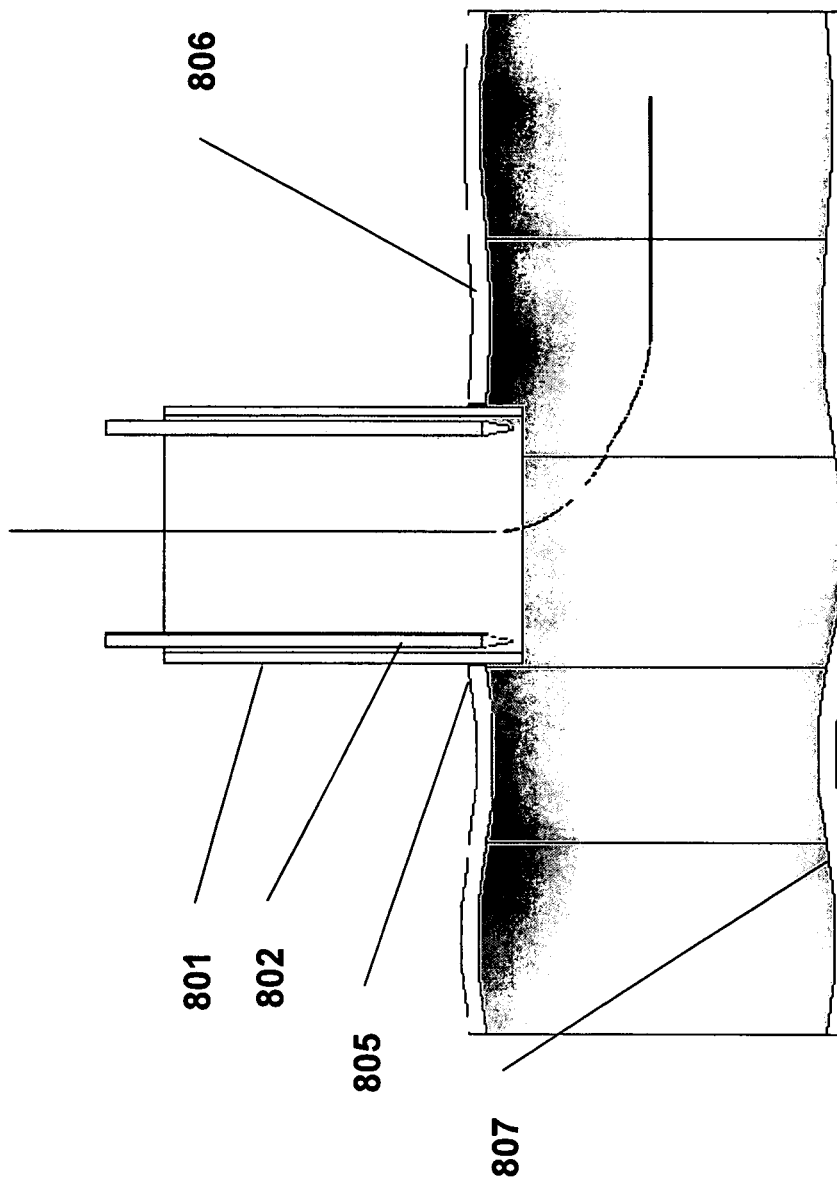

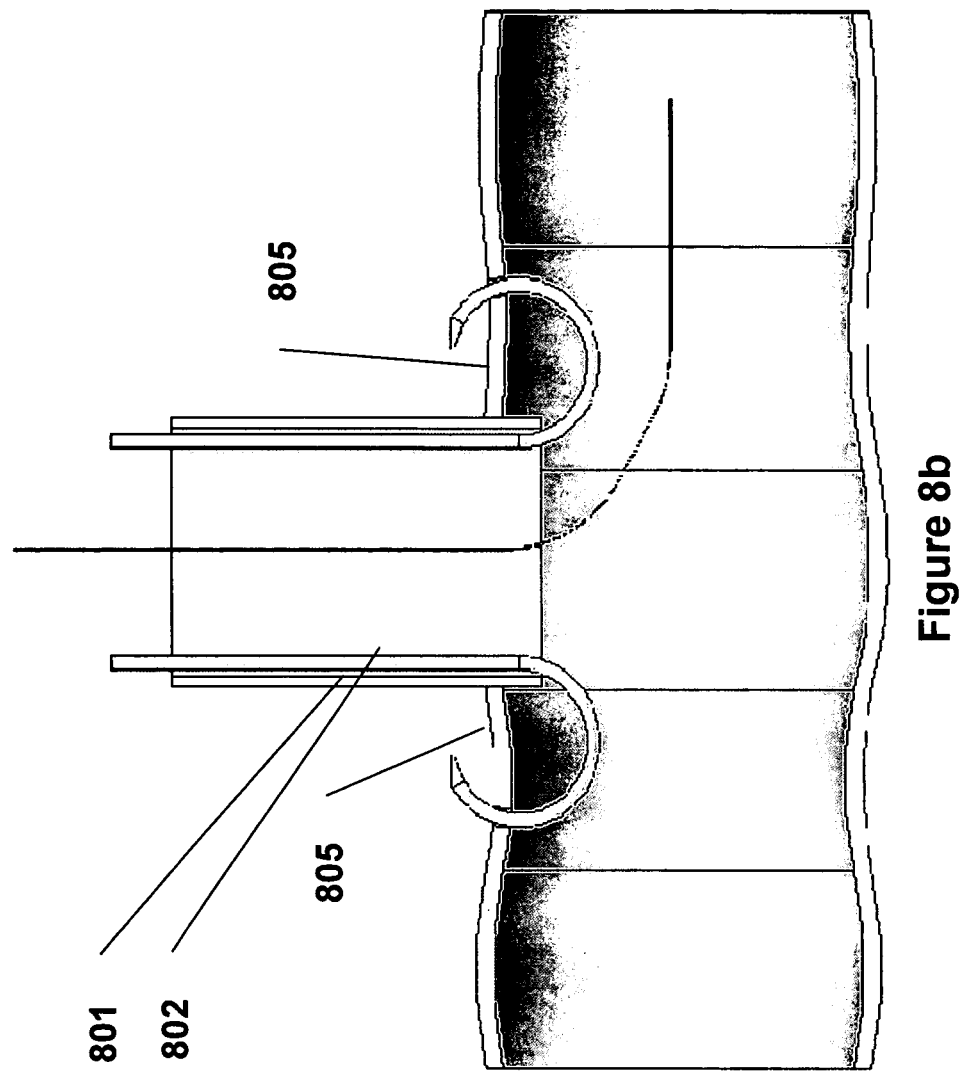

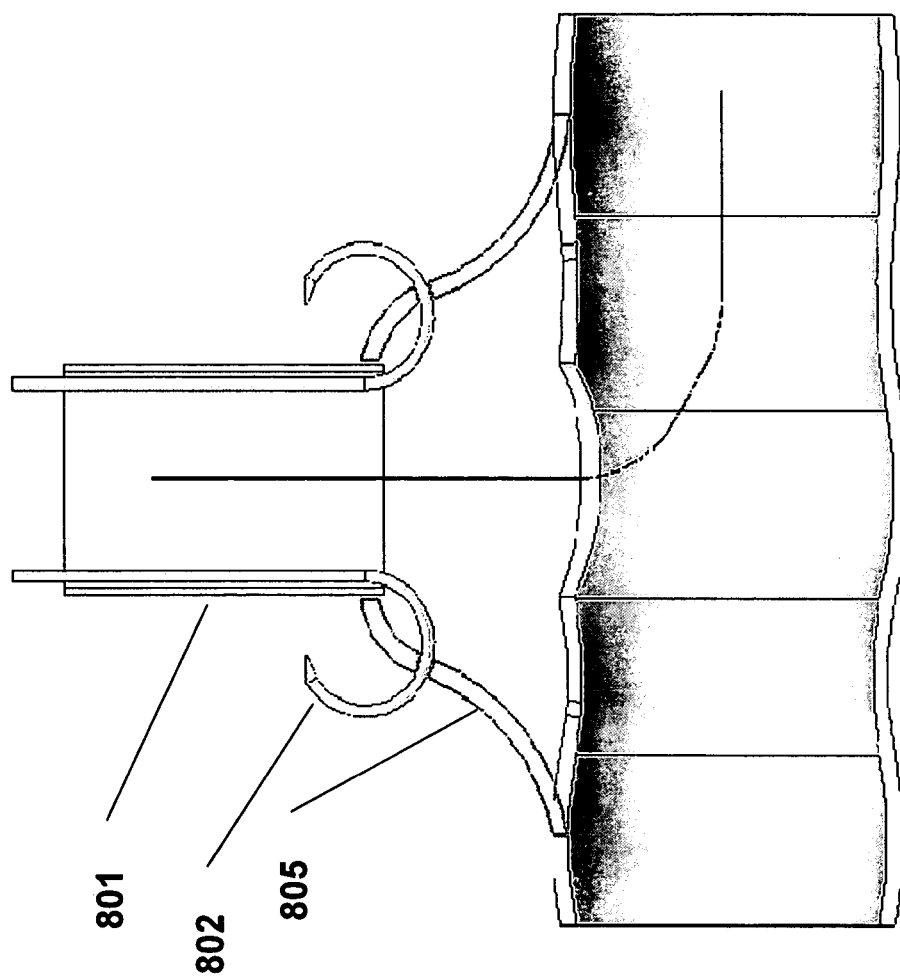

VASCULAR CLOSURE METHODS AND APPARATUSES

CROSS-REFERENCE TO RELATED APPLICATION

This application claims priority to U.S. provisional application 60/711,279, filed Aug. 24, 2005, and is a continuation-in-part of U.S. utility application Ser. No. 11/316,775, filed Dec. 23, 2005, now abandoned each of which is incorporated herein by reference.

FIELD OF THE INVENTION

The present invention relates to methods and apparatuses for closing punctures and apertures in human and animal tissue and to methods and apparatuses for inserting such an apparatus into such tissue to perform such closure functions.

BACKGROUND

During angiography and related procedures, catheters are inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, plaque removal, and infusion of a therapeutic substance. After the procedure is completed and the catheter is removed from the patient, the access hole must be closed to prevent massive hemorrhage. This is conventionally achieved by applying pressure over the blood vessel manually and then by applying a pressure bandage, compressive weight, or clamp device. With conventional methods, the rate of post-puncture hemorrhage is high, which causes considerable complications. This complication is exacerbated by the concomitant use of anticoagulant medications such as heparin or warfarin and by antiplatelet drugs, which are commonly used to treat vascular disease.

Sutures have been used to close access puncture wounds in blood vessels. U.S. Ser. No. 05/613,974 describes a device and method for applying sutures to a vascular puncture. US2004/0093027A1 describes barbed suture-like material that apposes the puncture site. US2005/0121042 A1 describes a device and method for applying suture to a vascular puncture. Difficulties with these methods include the large number of steps necessary to deploy the needles, capture the suture, withdraw the suture, tie the knot, and cut the suture. In addition, the hole in the blood vessel is often widened by insertion of the instrument, and the suture remains intravascularly on the endothelial surface, and thus can be a nidus for thrombus or intravascular mural hyperplasia with later spontaneous and catastrophic closure of the vessel.

Extravascular plugs have also been proposed for closure of vascular punctures. U.S. Ser. No. 05/254,105 and U.S. Ser. No. 05/330,445 describe an extravascular plug which is slid down the external surface of the catheter or introducer and is placed into the puncture site in this manner. U.S. Ser. No. 05/643,318 relates to a similar device that has its own vessel locator device. US22022822A1 and US2004/0158287A1 describe an extravascular plug that is delivered with a specialized system. US24215232A1 describes an extravascular plug with an intravascular anchor set with a sheath with a detection port. US2005/0085855A1 describes an extravascular collagen plug, held in place with an intravascular anchor, and a device that locks over a piece of suture. U.S. Ser. No. 05/906,631 describes a plug made of hydrophilic material. U.S. Ser. No. 06/126,675 describes an intravascular anchor and a bioabsorble extravascular plug. U.S. Ser. No. 06/623,509 describes a bioabsorbable plug. U.S. Ser. No. 06/296,657 and U.S. Ser. No. 06/743,195 describe an inflatable balloon that puts pressure on the puncture site. U.S. Ser. No. 06/569,185 describes an injectable vascular plug. U.S. Ser. No. 06/663,655 describes a plug that screws in the puncture tract. US2004/0143290 A1 describes a combination of an intraluminal balloon and injectable sealant. Disadvantages to these methods are related to the high likelihood of thrombosis associated with the intravascular plug or anchor, and the presence of collagen or other bioabsorble materials which cause inflammation, activate the clotting cascade, and increase the likelihood of thrombosis, which, in an arterial system, is catastrophic.

Vascular patches have also been used for repairing blood vessels, but usually only for large areas of damage. U.S. Ser. No. 05/100,422 describes a vascular patch that is sutured to the external surface of the damaged blood vessel. U.S. Ser. No. 05/100,422 describes a vascular patch achieved by instilled adhesives and the device for doing such. These are generally impractical for catheter-based methods. U.S. Ser. No. 06/248,124 and U.S. Ser. No. 05/507,744 describe devices and methods that use electrocautery for sealing vascular punctures. This also requires a complicated device, and perforation and thrombosis are very real possibilities.

Vascular clips or staples delivered through a catheter device have also been proposed. These devices have penetrating members that bring the edges of the tissue together. U.S. Ser. No. 06/695,867 describes a clip or staple that is delivered by a specialized device. U.S. Ser. No. 06/749,622 describes a number of different clips with sharpened barbs or ends that include both intra- and extravascular portions, made of metal with memory characteristics. U.S. Ser. No. 05/861,005 describes an arterial staple that is delivered with a specialized device. U.S. Ser. No. 05/919,207 describes a stapling system based on long hooked wires that appose the surfaces, with a small staple gun to close the lesion. U.S. Ser. No. 06/022,372 describes a similar staple gun. U.S. Ser. No. 06/296,657, U.S. Ser. No. 06/663,655, and U.S. Ser. No. 06/749,621 describe a clip that is external to the vessel, but clips the two sides of the puncture together, and a device for achieving such. U.S. Pat. No. 5,782,861 and U.S. Pat. No. 5,964,782 describe clip devices composed of two or more prongs or hooks that, depending on the direction of the prongs, can clip together the puncture site from the intra- or extravascular position, through the use of a collar which forces the prongs together or other mechanisms. These clip devices are composed of thick semi-rigid material, and can be placed only with a specialized instruments, and because of the rigidity have great potential to injure or cut the blood vessel. Disadvantages of these clip devices in general include difficulty in retrieving the device if misplaced, excessive manipulation required, the thickness of the clip material which tends to cut or shear the blood vessel, the large forces that must be used to curve the staples and fix the clips, the increased possibility of tearing the blood vessel, and the general lack of control of the forces being applied to the blood vessel.

Accordingly, there is a need for methods and apparatuses that are suitable for closure of vascular punctures or other openings, and that do not suffer from the drawbacks of conventional approaches.

SUMMARY OF THE INVENTION

The present invention provides methods and apparatuses that are suitable for closure of vascular punctures or other openings, and that do not suffer from the drawbacks of conventional approaches.

An apparatus according to the present invention can comprise a base member, defining an opening of sufficient cross-section to allow passage of a sheath through the opening. This allows the apparatus to be conveyed to the tissue opening using a conventional sheath. A plurality of active members mount with the base member, where each active member mounts with the base member and is capable of first and second configurations. In the first configuration, the active members are spaced apart such that they can be delivered using a conventional sheath, and such that the spacing is sufficient to span a portion of the tissue opening to be closed. In the second configuration, the active members move toward each other (relative to the first configuration), urging tissue placed between the active members into apposition. In operation, the apparatus can be delivered using a conventional sheath, with the active members in the first configuration. At the site of the tissue opening, the active members can engage tissue around the opening, and then be placed in the second configuration; for example by moving the active members relative to the sheath such that the sheath no longer props the active members apart. The tissue engaged by the active members is urged into apposition by the motion of the active members assuming the second configuration, closing the tissue opening.

Apparatuses according to the present invention can provide a catheter-delivered clip comprising fine, strong, but flexible material that after delivery contracts on the wound edges of a blood vessel so that individual members of the clip extend beyond the catheter edges and/or puncture dimensions. As the catheter is withdrawn, the edges of the tissue opening (e.g., a puncture wound) go from inversion (facing intravascularly) to eversion (facing extravascularly) preparing the wound edges for delivery of the clip. The clip delivery sheath can be advanced over the catheter and guidewire until the site of puncture of the blood vessel is reached. The delivery sheath can be pushed against the exterior of the blood vessel so that the everted edges of the wound are just interior to the delivery sheath. Using an exterior pushing sheath which goes around the delivery sheath, the clip can be pushed off the delivery sheath. The feet of clip can have textured, hooked grasping devices on the ends of the members, which seize the exterior of the vessel wall and urge the edges together.

The use of a plurality of fine and flexible nature the members can close tissue opening with low shear force applied to the blood vessel. As the clip is pushed off the delivery sheath the feet contract together and bring the blood vessel puncture wound edges together. If there is no blood leakage through the closure and the device is properly positioned and stable, then first the catheter and then the guidewire can be removed and the retaining sutures or strings loop cut, resulting in complete and rapid closure, which can then heal.

Since the present invention brings the puncture edges together, there can be true blood vessel healing with little endothelial disruption, reducing the chances of thrombosis or intimal hyperplasia. The device can be supplied in different diameters (french) to accommodate different sizes of catheters and different sizes of puncture holes. The present invention can provide apparatuses that are both contractible and retrievable (e.g., because of misplacement). In addition, although the example embodiments described herein generally have linear members, these members need not be strictly linear, but can assume a number of complex geometrical shapes and structural patterns without departing from the scope of the present invention.

Devices according to the present invention can utilize a contractible material, for example with memory characteristics, that allow the members of the device to close spontaneously on a puncture wound of a blood vessel. Members of such devices can have textured gripping surfaces, tissue hooks, or penetrators, to seize the vessel wall and stabilize the device. Such devices can use the spontaneous closing characteristic to seize the edges of the puncture site, and close them, resulting in a complete vascular closure. Such devices can be kept in an expanded state (high energy state of a memory material) by a delivery sheath and assume its functional, closing form (low energy state of a memory material) when pushed off a delivery sheath.

The present invention also comprises methods for closing tissue openings, comprising everting the edges of a tissue opening, then placing a device according to the present invention near the everted edges. The device can then be pushed off its delivery sheath, allowing the active members of the device to engage the tissue and bring the edges of the opening into apposition.

BRIEF DESCRIPTION OF THE FIGURES

The invention is explained by using embodiment examples and corresponding drawings, which are incorporated into and form part of the specification.

FIG. 1($a,b$) is a schematic illustration of an external vascular closure clip according to the present invention.

FIG. 2($a,b$) is a schematic illustration of an external vascular closure clip according to the present invention.

FIG. 3($a,b$) is a schematic illustration of an external vascular closure clip according to the present invention.

FIG. 7($a,b,c$) is a schematic illustration of eversion of the edges of a tissue opening using a device according to the present invention.

DETAILED DESCRIPTION

Figure 4A:
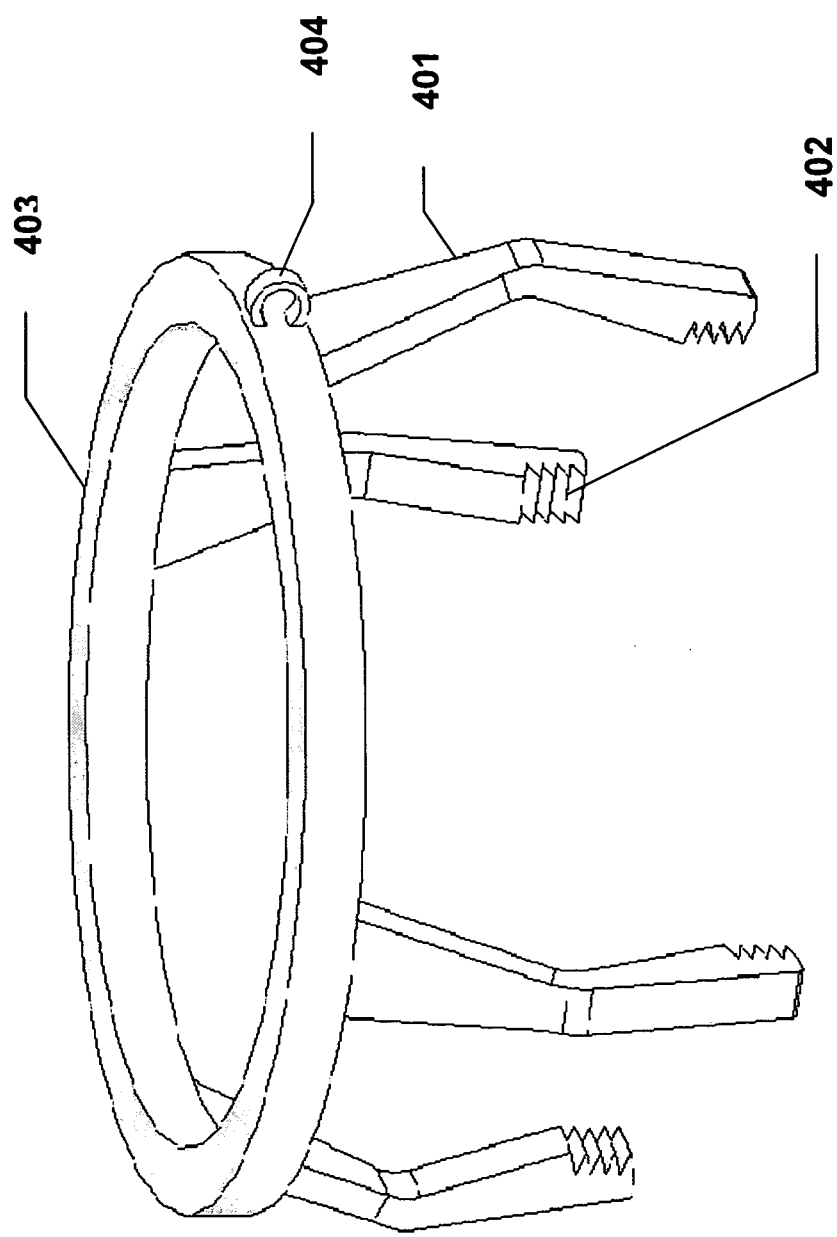
FIG. 4($a,b,c$) is a schematic illustration of an external vascular closure clip according to the present invention.

The present invention provides apparatuses and methods for closing a vascular puncture wound or any tissue aperture, for example those resulting from the insertion of a vascular catheter or surgical instrument, trauma or disease. The present invention embraces both apparatuses and methods for closing tissue openings such as vascular punctures. Devices according to the present invention can be open on a delivery sheath and when pushed off the sheath assume a closed position. This behavior can be provided by forming at least a portion of the device of a memory metal or material. The stress free state corresponds to the state at which the apparatus has closed upon the everted edges of a puncture wound of a blood vessel, and the stressed state is when the device is open and seated on the delivery sheath. Example embodiments of tissue closure apposition devices according to the present invention are shown in FIGS. 1, 2, 3, and 4. The descriptions may refer to "vessels" for convenience; the present invention is applicable to facilitate closure of various types of tissue openings.

FIG. 1(a,b) is a schematic illustration of an external vascular closure clip with multiple members. FIG. 1a is a lateral view of a vascular closure clip in the open state (high energy state); FIG. 1b is a lateral view of the same device in closed state (low energy state). The device comprises a base member 103, shaped to allow passage of a delivery sheath (not shown) through the base member 103. A plurality of active members 101 mount with the base member 103. A portion 102 of each active member 101 has a tissue engagement feature; in the figure shown as serrations formed in the end of the member 101.

In FIG. 1a, the active members 101 are spaced apart, allowing passage of a delivery sheath (not shown) between the active members 101. As an example, if the device is placed on a delivery sheath, the delivery sheath can hold the active members 101 apart. In FIG. 1b, the active members 101 have moved toward each other, urging tissue engaged by the tissue engagement features into apposition. As an example, if the device is pushed past the edge of a delivery sheath, the delivery sheath will no longer hold the tissue engagement features 102 of the active members 101 apart, and the resiliency or memory characteristics of the active members 101 can urge the tissue engagement features 2 towards each other. A hook, open or closed loop 104 for string or suture or for retrieval can mount with the device, for example with the base member 103 as shown in the figure.

The figure presents for illustration purposes 4 active members; the device can comprise as few as two active members, and as many as are practical within applicable design considerations. The tissue engagement features, shown as serrated portions of the active members in the figure, can comprise textured portions or attachments, mating portions with apposing feet, penetrating devices, hooks, teeth, or other adaptations to allow firm grip of the tissue. The base member is shown in the figure as a complete circular or cylindrical band; the base member can also be an incomplete band to accommodate better grip of a delivery sheath, and can comprise memory materials to increase the grip on the delivery sheath, and to assume a lower profile when delivered.

FIG. 2(a,b) is a schematic illustration of an external vascular closure clip with two members. FIG. 2a is a lateral view of a vascular closure clip with two members in the open state (high energy state). FIG. 2b is a lateral view of the clip in the closed state (low energy state). The device comprises a base member 203, shaped to allow passage of a delivery sheath (not shown) through the base member 203. A plurality of active members 201 mount with the base member 203. The active members 201 mount with tissue engagement members 205. The figure shows two active members 201 per tissue engagement member 205; any number of active members 201 can mount with each tissue engagement member 205. The tissue engagement members 205 comprise a tissue engagement feature 202, shown in the figure as a serrated portion of a side of the tissue engagement member 205 facing other tissue engagement members 205. A portion 202 of each active member 201 has a tissue engagement feature; in the figure shown as serrations formed in the end of the member 201.

In FIG. 2a, the active members 201 are spaced apart, allowing passage of a delivery sheath (not shown) between the active members 201. As an example, if the device is placed on a delivery sheath, the delivery sheath can hold the tissue engagement members 205 apart. In FIG. 2b, the active members 201 have flexed, moving the tissue engagement members 205 toward each other, urging tissue engaged by the tissue engagement features 202 into apposition. As an example, if the device is pushed past the edge of a delivery sheath, the delivery sheath will no longer hold the tissue engagement members 205 apart, and the resiliency or memory characteristics of the active members 201 can urge the tissue engagement members 205 towards each other. A hook, open or closed loop 204 for string or suture or for retrieval can mount with the device, for example with the base member 203 as shown in the figure. The tissue engagement members 205 allow gripping of the tissue along a greater surface than the example of FIG. 1(a,b). The tissue engagement members 205 can comprise a resilient or memory material, allowing them to conform to the shape of a delivery sheath while mounted with such a sheath, then to conform to the shape of another tissue engagement member 205 when gripping tissue (e.g., in FIG. 2b the tissue engagement members 205 present substantially straight and mutually parallel surfaces to each other).

FIG. 3(a,b) is a schematic illustration of an external vascular closure clip with penetrating grips. FIG. 3a is a lateral view of a vascular closure clip with two active members 301 in the open state (high energy state). FIG. 3b is a lateral view of the clip in the closed state (low energy state). The example of FIG. 3 is similar to that of FIG. 2. In FIG. 3, however, the tissue engagement features 306,307 comprise penetrating members 307 mounted or formed with one tissue engagement member 305, and corresponding depressions or openings 306 on a facing tissue engagement member 305. A hook, open or closed loop 304 for string or suture or for retrieval can mount with the device, for example with the base member 303 as shown in the figure.

Figure 4C:
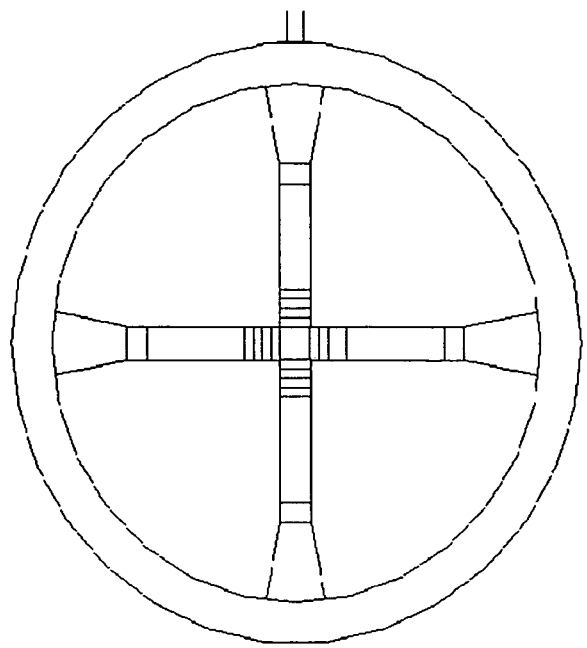
Figure 4B:
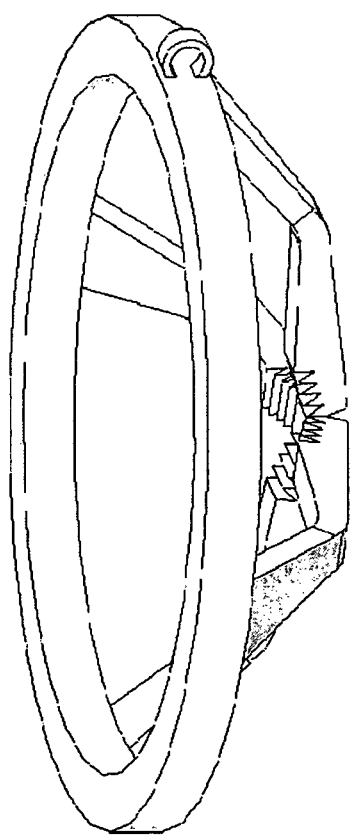

FIG. 4(a,b,c) is a schematic illustration of an external vascular closure clip with a low profile. FIG. 4a is a lateral view of a vascular closure clip in the open state (high energy state). FIG. 4b is a lateral view of the clip in the closed state (low energy state). FIG. 4c is a top view of the clip in the closed state (low energy state). The arrangement and operation of the clip in the figure is similar to that described in relation to FIG. 1, except that the active members 401 (having tissue engagement features 402) are configured to have a lower profile when deployed. This can be useful when the height of the deployed clip relative to the tissue surface is of concern. The active members 401 can also be configured to be substantially planar with the base member 403 when deployed, and can also be inverted so that, when deployed, the base member 403 is closer to the tissue wall than are the active members 401. A loop 404 for removal can mount with the base member 404. The active members 401 can also comprise other shapes to achieve the desired low profile. As an example, the active members can comprise members extending from the base member toward the center of the base member roughly in the plane of the base member, analogous to an iris diaphragm. As another example, the active members can be arranged like spokes, with the base member as the rim, where the spokes define an inner cross-section that is held open before deployment, and that is reduced by action of the spokes when the device is deployed. As another example, the active members can comprise members of variable length, mounted with the base member and extending roughly radially inward from the base member. The active members can be constrained to a shortened length before deployment, and allowed to lengthen (reducing the area between the active members) when deployed.

Figure 5A:
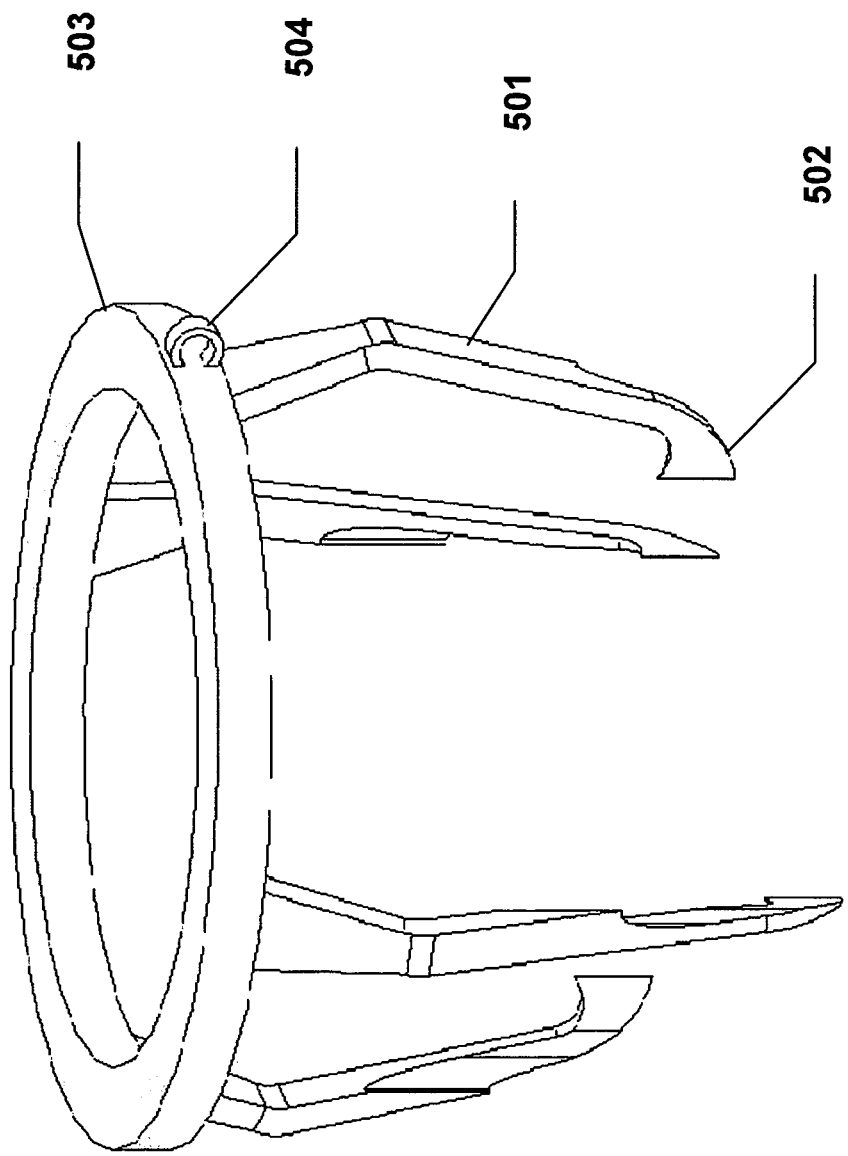
FIG. 5($a, b, c$) is a schematic illustration of an external vascular closure clip according to the present invention.
Figure 5C:
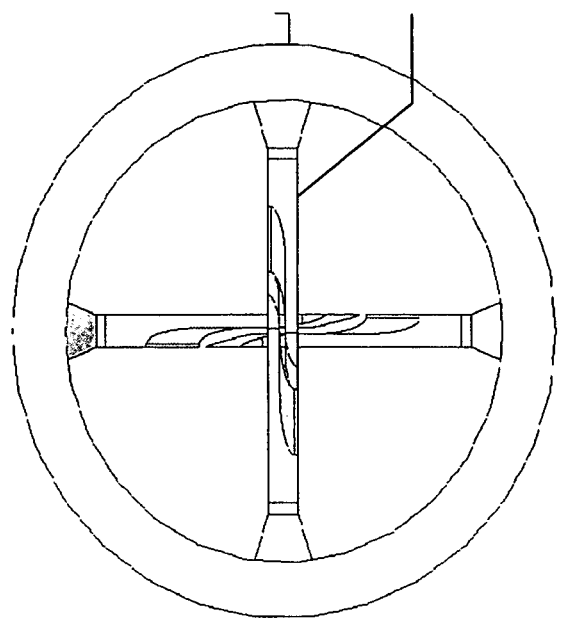
Figure 5B:
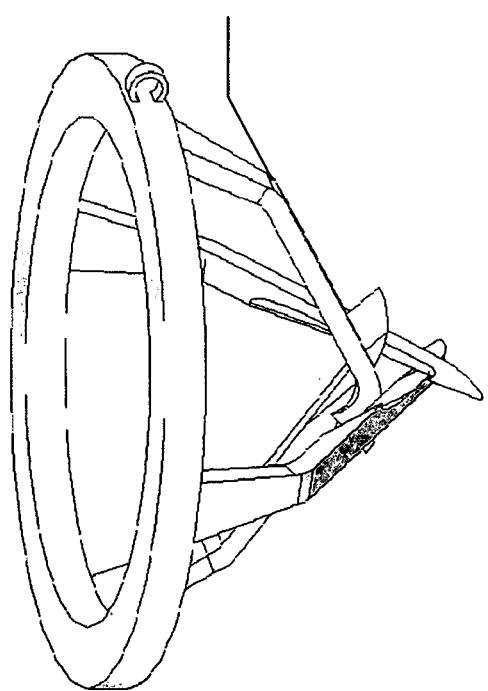

FIG. 5(a,b,c) is a schematic illustration of an external vascular closure clip with penetrating grips. FIG. 5a is a lateral view of a vascular closure clip device in the open state (high energy state). FIG. 5b is a lateral view of the clip in the closed state (low energy state). The structure and operation of the device in FIG. 5 is similar to that described in relation to FIG. 1, with a loop 504, extending from a base member 503, which can facilitate removal of the device. In the device of FIG. 5, however, then tissue engagement features 502 comprise portions of the active members 501 adapted to penetrate the tissue, in the figure sharpened ends of the active members. Penetration of the tissue by the ends of the active members 502 can facilitate more certain anchoring of the clip when deployed. The active members can also comprise more complicated shapes and relationships among the active members, e.g., spirals, cross-overs, barbs, and complete or incomplete twists and turns, all which can be determined by the characteristics of the material and the desired tissue binding forces.

For simplicity of illustration, the previous embodiments were depicted with wire-like active members. The active members can comprise other shapes and materials. As an example, active members can be made with polymers, covered with polymers, and comprise drug-eluting material. The active members or base member, or both, can be covered with fabric or backing or other material, including bioreabsorbable material, to further plug the puncture tract. The active members can comprise loops of wire, filaments, struts, beams, patterns, woven elements, continuous or non-continuous materials, or other geometric structures.

Any part of an apparatus according to the present invention can be made from any of a number of suitable materials, or combinations thereof. In some applications, it can be desirable for members to be of radioopaque materials or be coated to be made radioopaque. Members can be made from bioabsorbable polymers or compounds, non-absorbable alloys and compounds including stainless steel, MP35, Nitinol, Nickel-Titanium alloy, Kevlar, nylon polyester acrylic, gold, platinum, tantalum, niobium, molybdenum, rhodium, palladium silver, hafnium, tungsten, iridium. Materials with memory can be useful, where the memory property can provide force for activation of the active members from the open to the closed state. Members can be made in the form of wires, fibers, filaments, small beams, and other extruded, woven, or formed shapes. Examples of suitable materials include piano wire, super elastic memory wire, chromium allows, alloys of titanium and nickel, and other elastic memory materials. A suitable fabric or coating can be made from a number of suitable materials; in some applications it can be desirable to use flexible polymeric materials with elastomeric properties including polyurethane, polyethylene, polyestenurethane, polyimide, olyethreimide, polycarbonate, polysiloxane, polyvinyls, hydroxyethylmethacrylate, related polymers, copolymers of these or other polymers, or drug-embedded or drug-eluting polymers to prevent coagulation or intimal hyperplasia (such as Taxol), which can be made radiopaque by markers to addition of appropriate radiopaque materials.

Figure 6B:
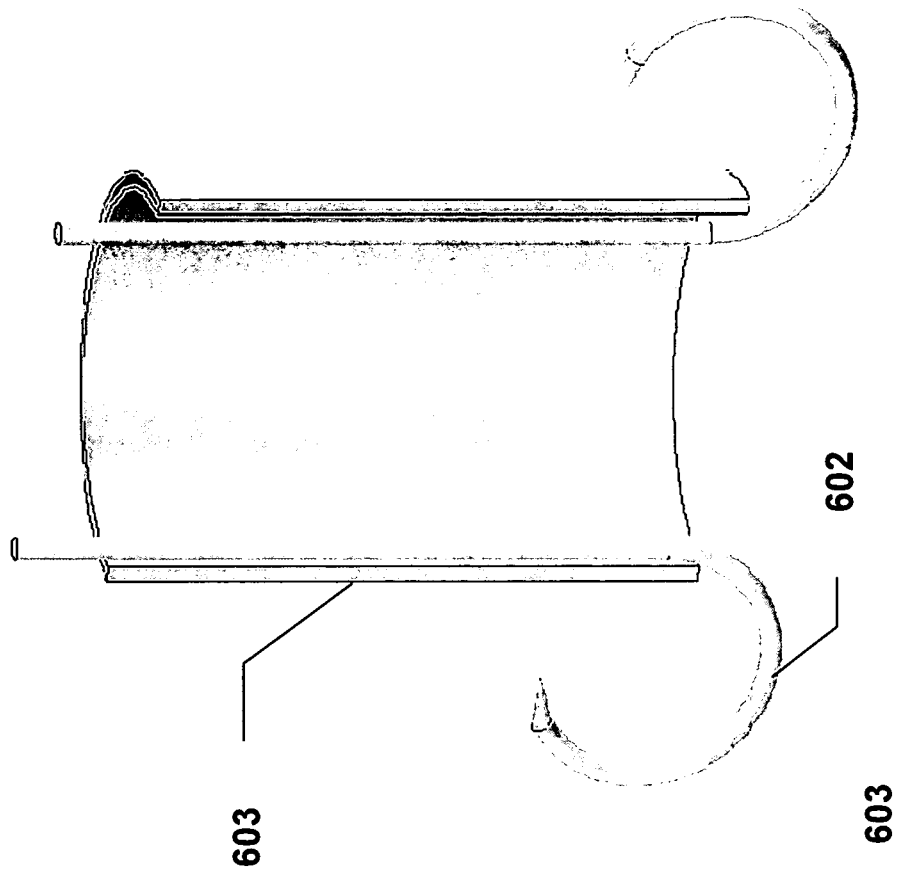
FIG. 6($a,b$) is a schematic illustration of a gripper and sheath according to the present invention.
Figure 6A:
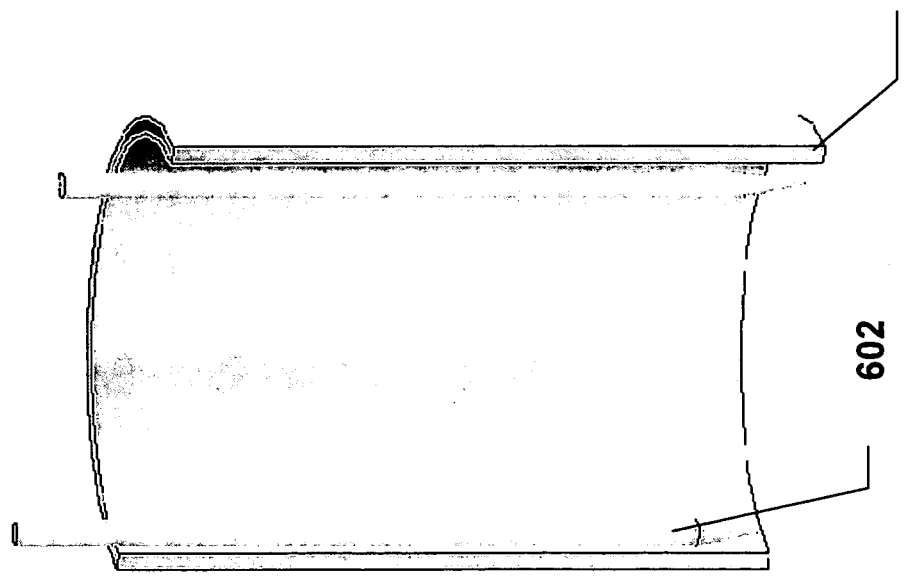

Devices according to the present invention can be placed on everted tissue edges (i.e., the edges of the opening are turned towards the device). Tissue edge eversion can be accomplished with a gripper or everter device, or by pulling back a sheath. FIG. 6(a,b) is a schematic illustration of a gripper and sheath, shown in section to illustrate gripper tines disposed within the sheath 603. Gripper tines 602 (two in the figure although more or fewer can be used) are disposed within a sheath 603 in FIG. 6a. The sheath 603 constrains the gripper tines 602 to fit within the walls of the sheath 603. In FIG. 6b, the gripper tines 602 have moved past the end of the sheath 603. Absent the constraining influence of the sheath 603, the gripper tines 602 have curved outwards from the sheath and upwards along the direction of the sheath. The gripper tines can grip the edges of a tissue opening, and evert them when the gripper tines or the corresponding sheath is pulled away from the tissue.

FIG. 7(a,b,c) is a schematic illustration of eversion of the edges of a tissue opening using a device such as that described in relation to FIG. 6. FIG. 7a shows the device with the gripper tines 702 constrained in a sheath 703. A guidewire 704 passes through the sheath 703. The sheath 703 is resident in the tissue opening, passing through the proximal vessel wall 706 but not reaching the distal vessel wall 705. FIG. 7b shows the device after the gripper tines 702 have been extended past the end of the sheath 703. The gripper tines 702, have curved away from the sheath 703 and back along the direction of the sheath 703, penetrating the proximal vessel wall 706. Traction applied to the gripper tines 702 and sheath 703 everts the edges of the opening, as shown in FIG. 7c. The edges are held by the gripper tines 702 so that the proximal vessel wall 706 is pulled when the gripper tines 702 and sheath 703 are pulled. The everted edges of the tissue opening are now ready for deployment of a clip like those described herein.

FIG. 8(a,b,c,d,e,f,g) is a schematic illustration of steps in a method of closing a tissue opening according to the present invention. In FIG. 8a, a gripper sheath 801, for example a gripper sheath like that described in relation to FIG. 7, is present within an opening in tissue, near a proximal wall 806 and edges 805 of an opening therethrough, but not near a distal wall 807. The gripper sheath 801 constrain gripper tines 802 disposed within the gripper sheath 801. In FIG. 8b, the gripper tines 802 have been extended past the end of the gripper sheath 801, curving back and engaging the edges 805 of the tissue opening. In FIG. 8c, the gripper sheath 801 has been pulled away from the tissue. The edges 805 of the opening, held by the gripper tines 802, have been everted by the motion of the gripper sheath 801. The gripper tines can reside within sublumens within or on the sheath, or a single shared lumen in the sheath. The number of gripper tines can be 2 or greater, and they can be directed away from the lumen or cross over each other. They can penetrate the blood vessel wall, but need not fully penetrate the vessel, instead simply gripping the vessel wall so it cab be everted. The tines can be extended by pushing or by a specialized instrument that provides suitable extension such as a gun-like or syringe-like plunger configuration.

Figure 8D:
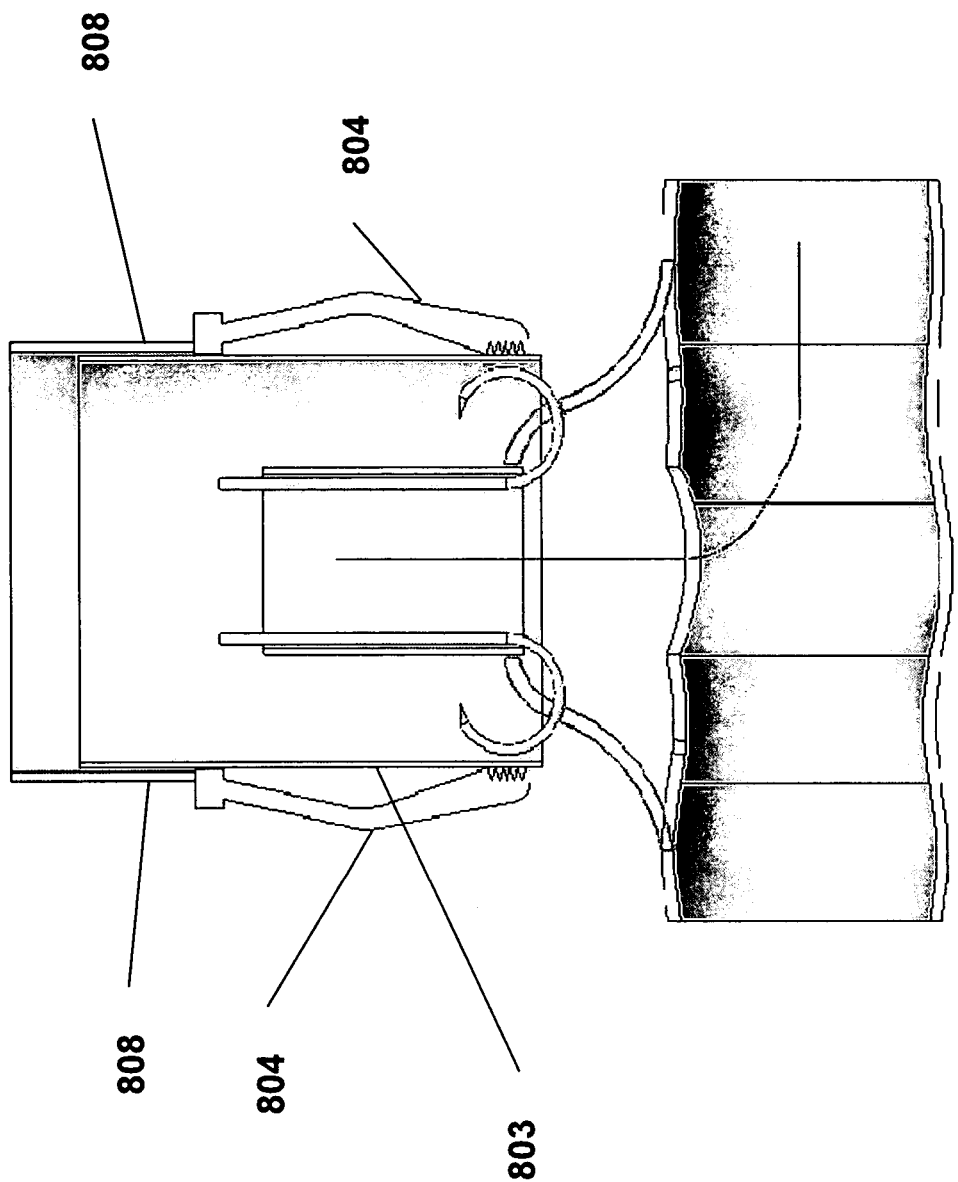
FIG. 8($a,b,c,d,e,f,g$) is a schematic illustration of steps in a method of closing a tissue opening according to the present invention.
Figure 8E:
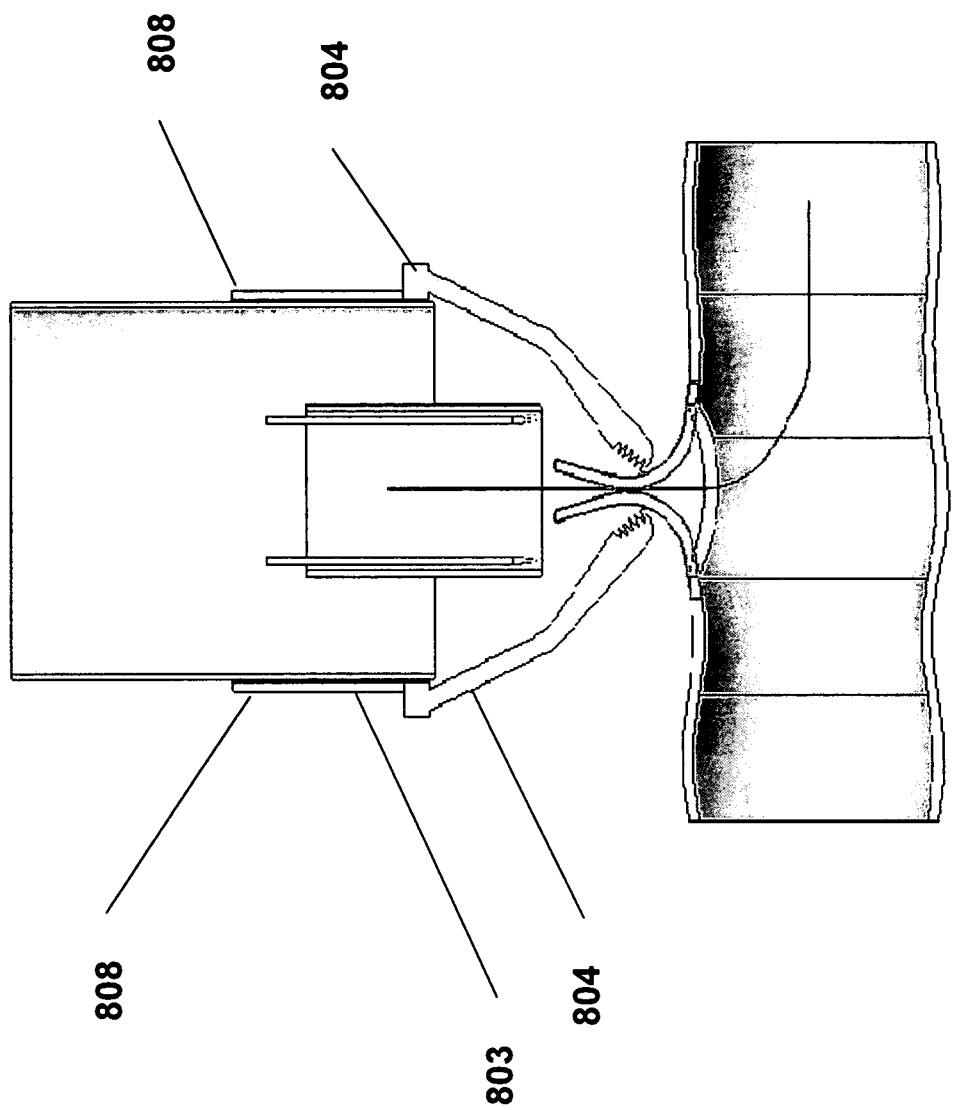
Figure 8F:
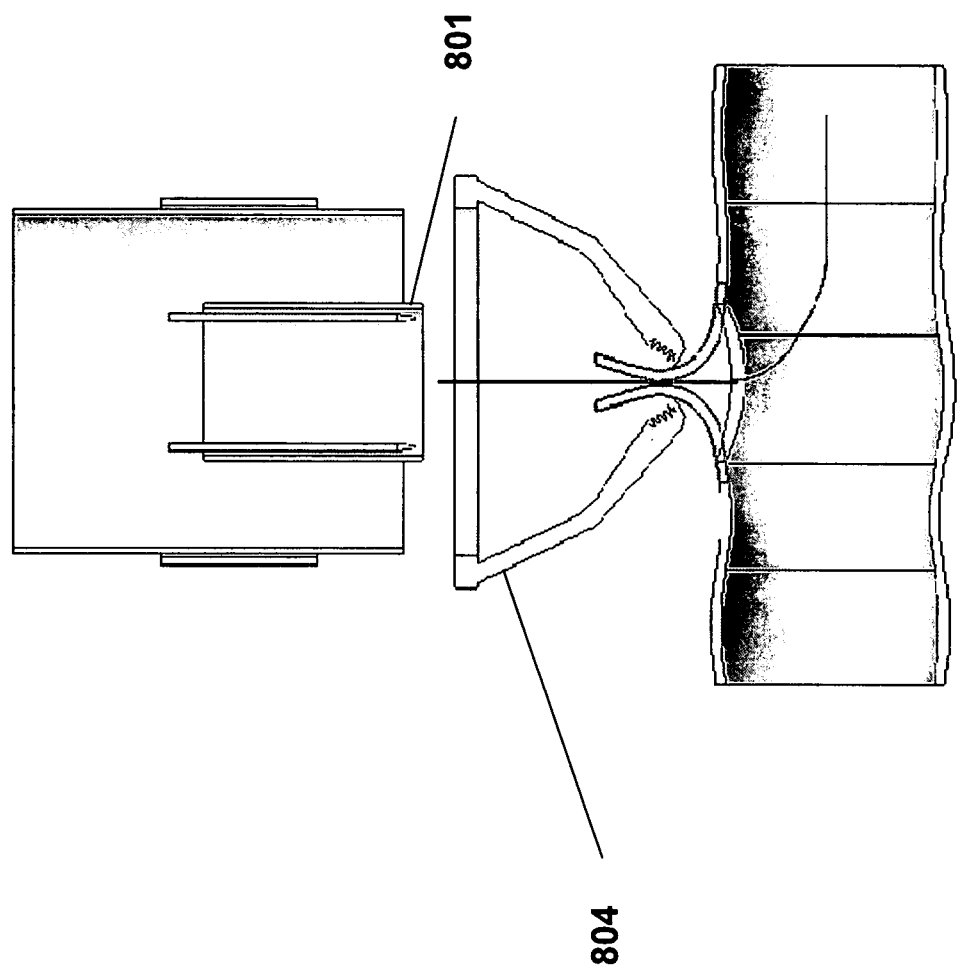
Figure 8G:
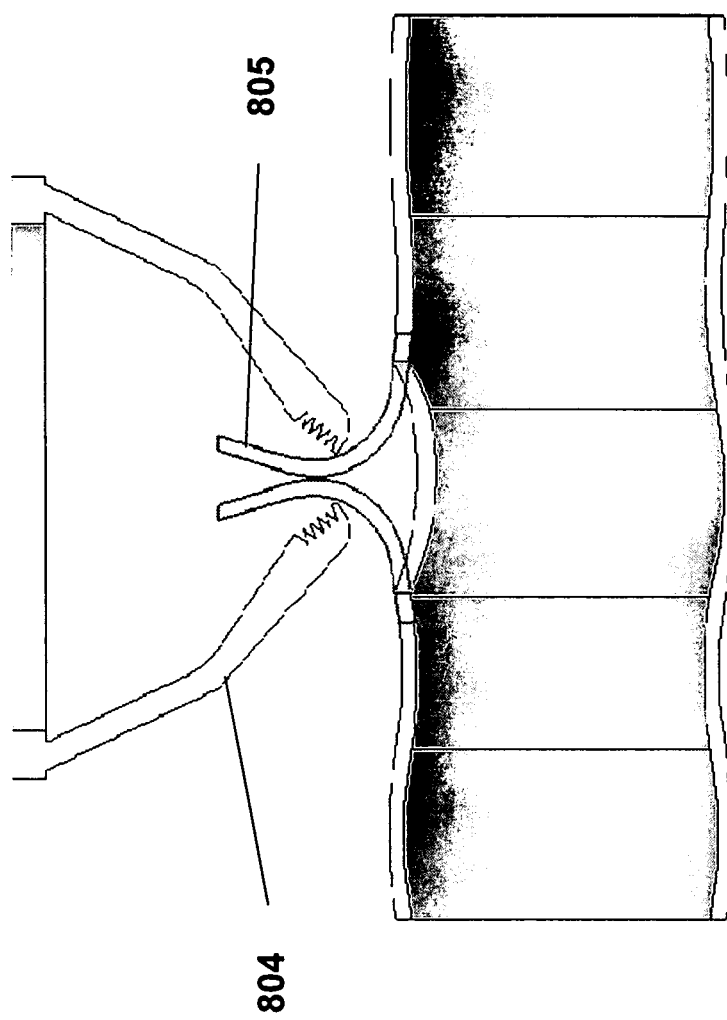

In FIG. 8d two additional sheaths are shown. A delivery sheath 803 has mounted with it a closure device 804 such as those described herein. A pushing sheath 808 is placed in relationship with the delivery sheath 803 such that the pushing sheath 808 can slide down the delivery sheath 803 and apply force to the device 804. If FIG. 8e the pushing sheath 808 has been pushed down the delivery sheath 803 a sufficient distance to force the device 804 past the end of the delivery sheath 803. As described previously in relation to device embodiments, the device, when free of the constraining influence of the delivery sheath 803, assumes a closed state wherein the device 804 urges the edges 805 of the opening into apposition. In FIG. 8f, the sheaths have been pulled away from the opening, leaving the device 804 engaged with the tissue and the edges of the opening held in apposition by the device 804. The tissue can be inspected at this stage to assess proper placement and operation of the device. If the opening has been appropriately closed, then the sheaths and guidewire can be removed, leaving the device 804 in place to hold the opening closed, as shown in FIG. 8g.

FIG. 9(a,b,c,d,e,f) is a schematic illustration of steps in a method of closing a tissue opening according to the present invention. In FIG. 9a, an operative catheter or sheath 901 is present within an opening in tissue, in contact with edges 905 of the opening. A device 904 such as those described herein mounts with a delivery sheath 903. In FIG. 9b, the operative catheter or sheath 901 has been pulled away from the tissue sufficient to evert the edges 905 of the opening. In FIG. 9c, a pushing sheath 908 has been introduced outside the delivery sheath 903, configure to transmit force to the device 904.

Figure 9B:
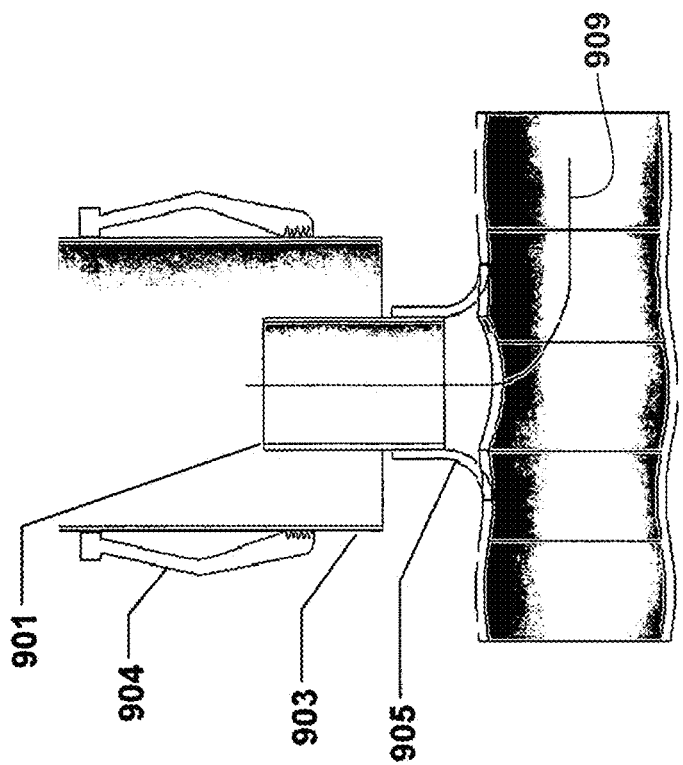
FIG. 9($a,b,c,d,e,f$) is a schematic illustration of steps in a method of closing a tissue opening according to the present invention.
Figure 9A:
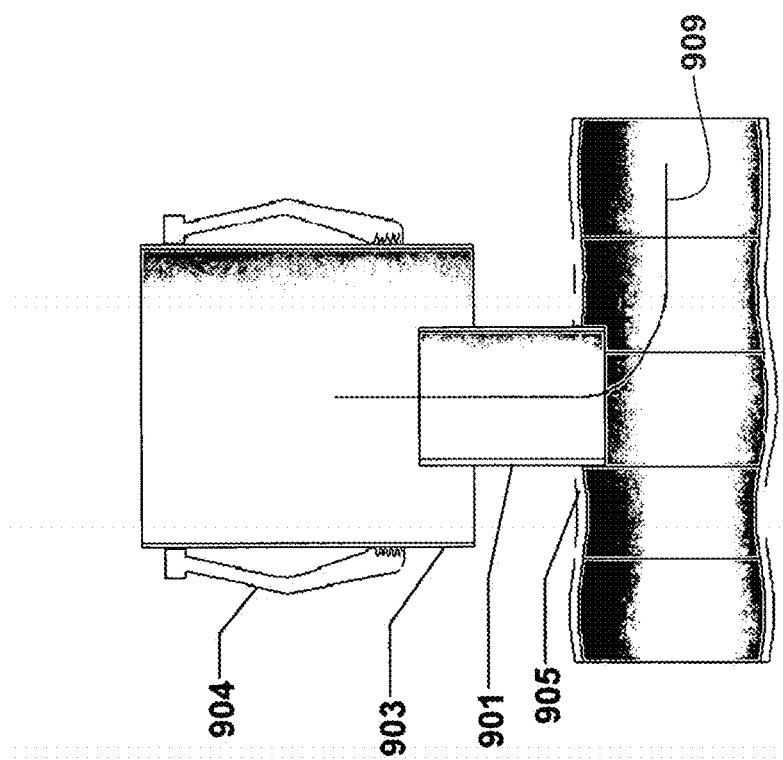
Figure 9D:
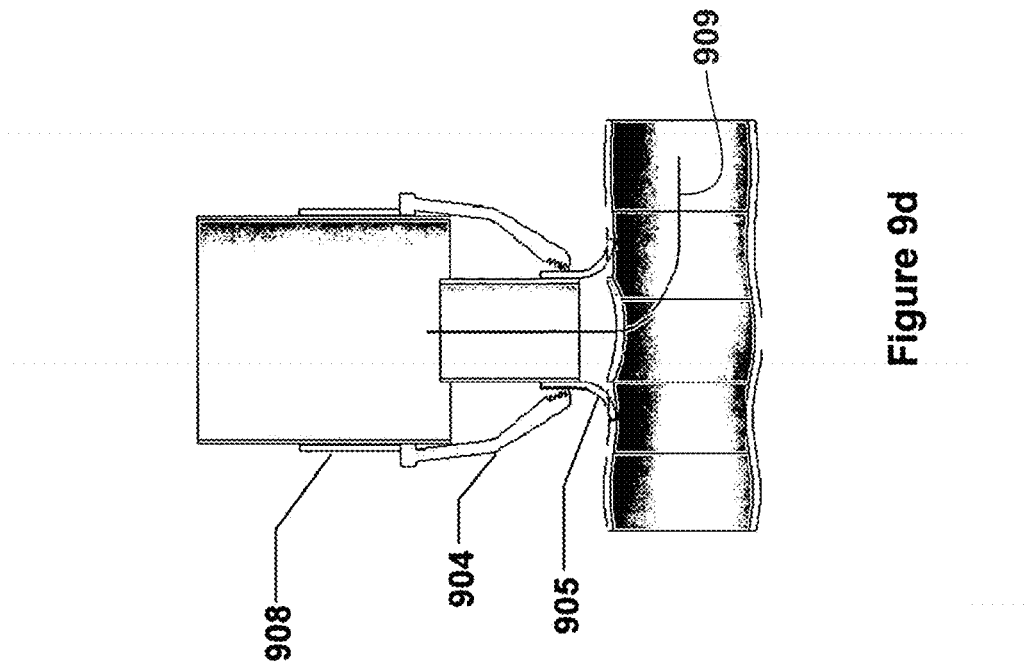
Figure 9C:
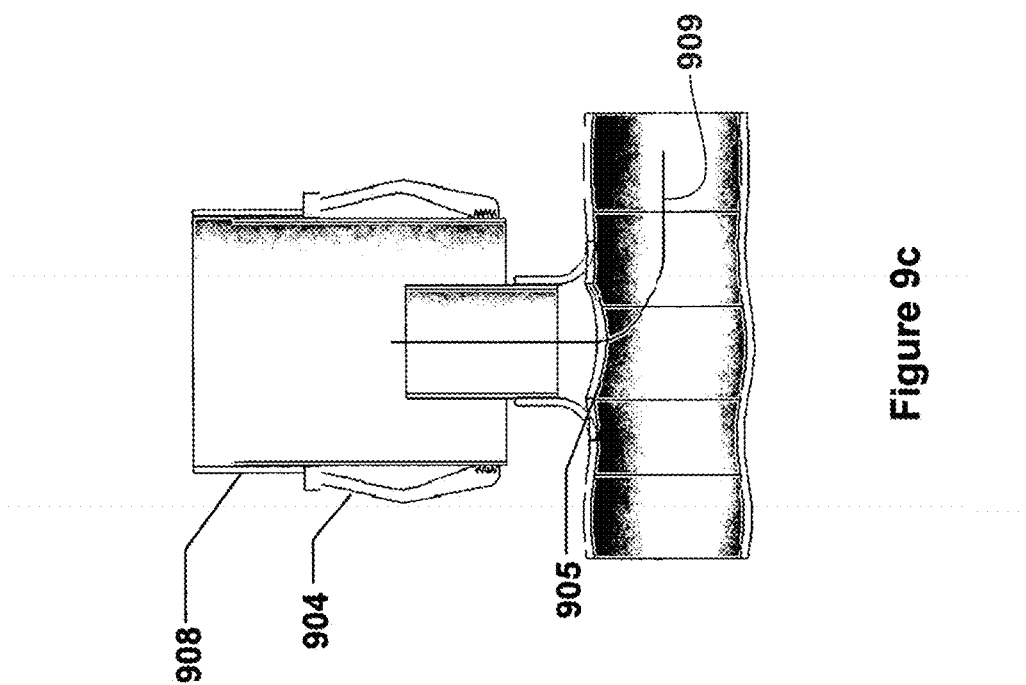
Figure 9F:
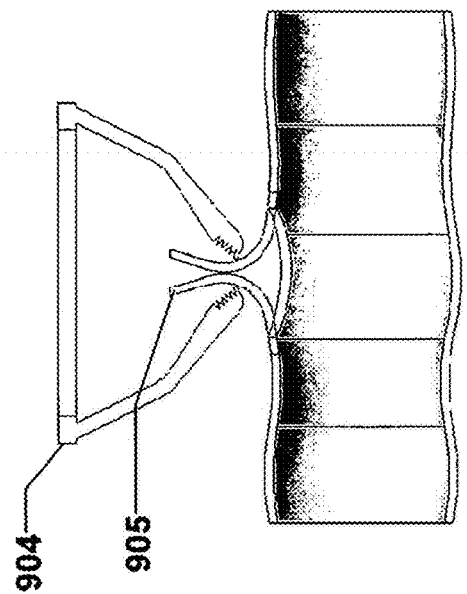
Figure 9E:
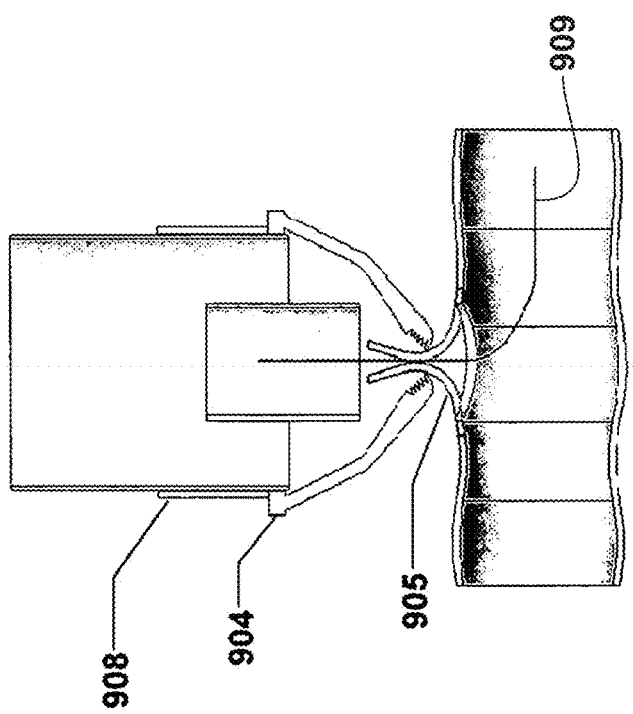

In FIG. 9d, the pushing sheath 908 has been used to push the device 904 past the end of the delivery sheath 903, but not yet past the end of the operative catheter or sheath 901. As described herein, the device can assume a closed state once free from the constraint of the delivery sheath 903. In the closed state, the device brings the edges 905 of the opening into apposition. In FIG. 9d, the device can be less than fully closed, since the operative catheter or sheath 901 is still in position to prevent full closure. In FIG. 9e, the operative catheter or sheath 901 has also been withdrawn relative to the device 904 and pushing sheath 908, allowing the device 904 to assume the closed state, bringing the edges 905 of the tissue opening into apposition. The tissue can be inspected at this stage to assess proper placement and operation of the device. If the opening has been appropriately closed, then the sheaths and guidewire 909 can be removed, leaving the device 904 in place to hold the opening closed, as shown in FIG. 9f.

The particular sizes and equipment discussed above are cited merely to illustrate particular embodiments of the invention. It is contemplated that the use of the invention may involve components having different sizes and characteristics. It is intended that the scope of the invention be defined by the claims appended hereto.

We claim:

1. A tissue closure device, comprising:
   (a) a base member, defining an opening of sufficient cross-section to allow passage of a sheath therethrough;
   (b) a plurality of active members extending from the base, each active member having a length, width and thickness and having a first portion adjacent the base and a second portion extending from the first portion towards an active member distal end,
      the first portion of the active member tapering in width from the base toward the second portion and extending away from a longitudinal axis of the base member in an open state,
      the second portion being spaced apart from the first portion and extending towards the longitudinal axis of the base member in the open state and tapering in thickness from the distal end of the active member towards the first portion; and
      wherein, the active members are configured to move from a first configuration to a second configuration, wherein when the active members are in the first configuration the active members are spaced apart sufficiently to allow passage of the sheath between the active members, and wherein when the active members are in the second configuration the active members urge tissue placed between the second portions of the active members into apposition.

2. The tissue closure device as in claim 1, wherein the active members changing from the first configuration to the second configuration comprises flexing of the active members.

3. The tissue closure device as in claim 1, wherein the active members assume the second configuration absent an external force applied to the active members.

4. The tissue closure device as in claim 1, wherein each active member comprises an elongated leg, that, when in the first configuration has the first and second portions lying along a line that does not intersect the axis of the sheath passed through the base member, and when in the second configuration has the first and second portions lying along a line that does intersect an axis of a sheath passed through the base element.

5. The tissue closure device as in claim 1, wherein a portion of the active members is substantially planar with the base member in the second configuration.

6. A tissue closure apparatus comprising:
   (a) a sheath, having walls defining an inner cross-section and an outer cross-section, the sheath having a distal end;
   (b) a base member, defining an opening of sufficient cross-section to allow passage of the sheath therethrough, mounted with the sheath at a location proximal the distal end of the sheath such that the base member can slide past an end of the sheath;
   (c) a plurality of active members extending from the base, each active member having a length, width and thickness and having a first portion adjacent the base and a second portion extending from the first portion towards an active member distal end,
      the first portion of the active member tapering in width from the base toward the second portion and extending away from a longitudinal axis of the base member in a stressed state,
      the second portion being spaced apart from the first portion, angularly orientated relative to the first portion, and extending towards the longitudinal axis of the base member in the stressed state and tapering in thickness from the distal end of the active member towards the first portion; and
      wherein, the active members are configured to move from a first configuration to a second configuration, wherein when the active members are in the first configuration the active members are spaced apart sufficient to allow passage of the sheath between the active members, and wherein when the active members are in the second configuration the active members urge tissue placed between the second portions of the active members into apposition.

7. The tissue closure device as in claim 6, wherein the active members changing from the first configuration to the second configuration comprises flexing of the active members.

8. The tissue closure device as in claim 6, wherein each active member comprises an elongated leg, that, when in the first configuration has the first and second portions lying along a line that does not intersect the axis of the sheath passed through the base member, and when in the second configuration has the first and second portions lying along a line that does intersect an axis of a sheath passed through the base element.

9. The tissue closure device as in claim 6, wherein the tissue engagement feature comprises a serrated portion.

10. The tissue closure device as in claim 6, wherein a portion of the active members is substantially planar with the base member when in the second configuration.

11. A device to close an opening in a blood vessel comprising a base member and a plurality of leg-like members extending from the base member and that in an open state can reside on a delivery sheath, and after being pushed from the delivery sheath assume a closed state, the leg-like members each having a length, width and thickness and having a first portion adjacent the base and a second portion extending from the first portion towards an active member distal end, the first portion tapering in width in a first taper direction from the base toward the second portion, the second portion having tissue engagement features and tapering in thickness from the distal end of the active member towards the first portion the first portion of the active member extending away from a longitudinal axis of the device in the open state and the second portion of the leg-like member being angularly orientated relative to the first portion and extending towards the longitudinal axis of the device in the open state, wherein in the closed state the tissue engagement features engage an everted vessel wall and urge the edges of the opening into apposition.

12. The device as in claim 11, wherein the leg-like members mount to a whole or partial ring.

13. The device as in claim 11, wherein the leg-like members mount to a complete cylindrical band.

14. The device as in claim 11, wherein the leg-like members comprise a material with memory characteristics.

15. The device as in claim 11, further comprising a loop-like retrieval fitting mounted with the ring.

16. The device as in claim 11, further comprising a fabric or membrane mounted with the leg-like members.

17. The device as in claim 11, wherein the leg-like members elute a therapeutic material or drug.

18. The device as in claim 11, wherein the leg-like members comprise angled dentates or tissue penetrators to discourage movement or migration of the device into the lumen of the blood vessel.

19. The device as in claim 11, wherein the tissue engagement features comprises serrated or textured portions.

20. The device as in claim 11, wherein the open state is a high energy state and the closed state is a low energy state.

* * * * *